US011179247B2

(12) United States Patent
Jebsen et al.

(10) Patent No.: US 11,179,247 B2
(45) Date of Patent: Nov. 23, 2021

(54) INTERVERTEBRAL IMPLANTS

(71) Applicant: Zimmer Biomet Spine, Inc., Westminster, CO (US)

(72) Inventors: Samuel Jebsen, Arvada, CO (US); Ryan Watson, Boulder, CO (US); Marc Bereau, Saint-Andre-les-Vergers (FR); Edouard Jouan, Lavau (FR)

(73) Assignee: Zimmer Biomet Spine, Inc., Westminster, CO (US)

(*) Notice: Subject to any disclaimer, the term of this patent is extended or adjusted under 35 U.S.C. 154(b) by 165 days.

(21) Appl. No.: 16/705,556

(22) Filed: Dec. 6, 2019

(65) Prior Publication Data

US 2020/0188130 A1 Jun. 18, 2020

Related U.S. Application Data

(60) Provisional application No. 62/778,543, filed on Dec. 12, 2018, provisional application No. 62/830,863, filed on Apr. 8, 2019.

(51) Int. Cl.
*A61F 2/44* (2006.01)
*A61F 2/30* (2006.01)

(52) U.S. Cl.
CPC ...... *A61F 2/447* (2013.01); *A61F 2002/3092* (2013.01); *A61F 2002/3093* (2013.01);
(Continued)

(58) Field of Classification Search
CPC .......... A61F 2/44; A61F 2/4455; A61F 2/446; A61F 2/4465; A61F 2/447;
(Continued)

(56) References Cited

U.S. PATENT DOCUMENTS 8,454,700 B2 6/2013 Lemoine et al.
9,662,226 B2 5/2017 Wickham
(Continued)

FOREIGN PATENT DOCUMENTS

| CN | 105559950 | 2/2018 |
|---|---|---|
| EP | 3406226 | 11/2018 |
| WO | 2017106780 | 6/2017 |

OTHER PUBLICATIONS

"European Application Serial No. 19215500.0, Extended European Search Report dated May 12, 2020", 9 pages.
(Continued)

*Primary Examiner* — Eric S Gibson
(74) *Attorney, Agent, or Firm* — Schwegman Lundberg & Woessner, P.A.

(57) ABSTRACT

An interbody implant can comprise a cage and a porous structure. The cage can comprise an anterior segment, a medial segment, a posterior segment and a lateral segment contiguously connected to each other to define an interior space. The porous structure can be located in the interior space and can be bounded by the cage. The porous structure can comprise opposed superior and inferior surfaces exposed through the cage, an internal cavity located in an interior of the porous structure, and a plurality of ports connecting the internal cavity to the superior and inferior surfaces. A superior-inferior stiffness of the interbody implant can be defined by the porous structure. The porous structure can be compressed within a patient by movement of the spine to biologically stimulate bone growth in vertebrae adjacent the interbody implant. The implant can be configured for lateral, anterior and posterior insertion at different spine levels.

24 Claims, 19 Drawing Sheets

(52) U.S. Cl.
CPC ............... *A61F 2002/30281* (2013.01); *A61F 2002/30433* (2013.01)

(58) Field of Classification Search
CPC .. A61F 2002/30014; A61F 2002/30158; A61F 2002/30261; A61F 2002/30266; A61F 2002/30281; A61F 2002/30593; A61F 2002/3092; A61F 2002/3093; A61F 2002/4495

See application file for complete search history.

(56) References Cited

U.S. PATENT DOCUMENTS

| | | | | |
|---|---|---|---|---|
| 10,842,645 | B2* | 11/2020 | Nebosky | ................. A61F 2/447 |
| 2005/0112397 | A1* | 5/2005 | Rolfe | .................. A61B 17/866 |
| | | | | 428/593 |
| 2005/0177238 | A1* | 8/2005 | Khandkar | ........... A61L 27/3834 |
| | | | | 623/17.11 |
| 2017/0333205 | A1* | 11/2017 | Joly | ....................... A61F 2/4455 |
| 2018/0104063 | A1 | 4/2018 | Asaad | |
| 2018/0110624 | A1 | 4/2018 | Arnone | |
| 2018/0161172 | A1* | 6/2018 | Nebosky | ................. A61F 2/447 |
| 2018/0193152 | A1* | 7/2018 | Bauer | ..................... A61F 2/447 |
| 2018/0256336 | A1 | 9/2018 | Mueller et al. | |
| 2019/0091027 | A1* | 3/2019 | Asaad | ..................... A61F 2/447 |
| 2020/0093612 | A1* | 3/2020 | Blain | .................... A61F 2/4611 |
| 2020/0188130 | A1* | 6/2020 | Jebsen | .................... A61F 2/447 |
| 2020/0297505 | A1* | 9/2020 | McLaughlin | ............. A61F 2/28 |
| 2021/0038403 | A1* | 2/2021 | Neary | ................. A61F 2/30771 |

OTHER PUBLICATIONS

"European Application Serial No. 19215500.0, Response filed Extended European Search Report dated May 12, 2020", 17 pages.

* cited by examiner

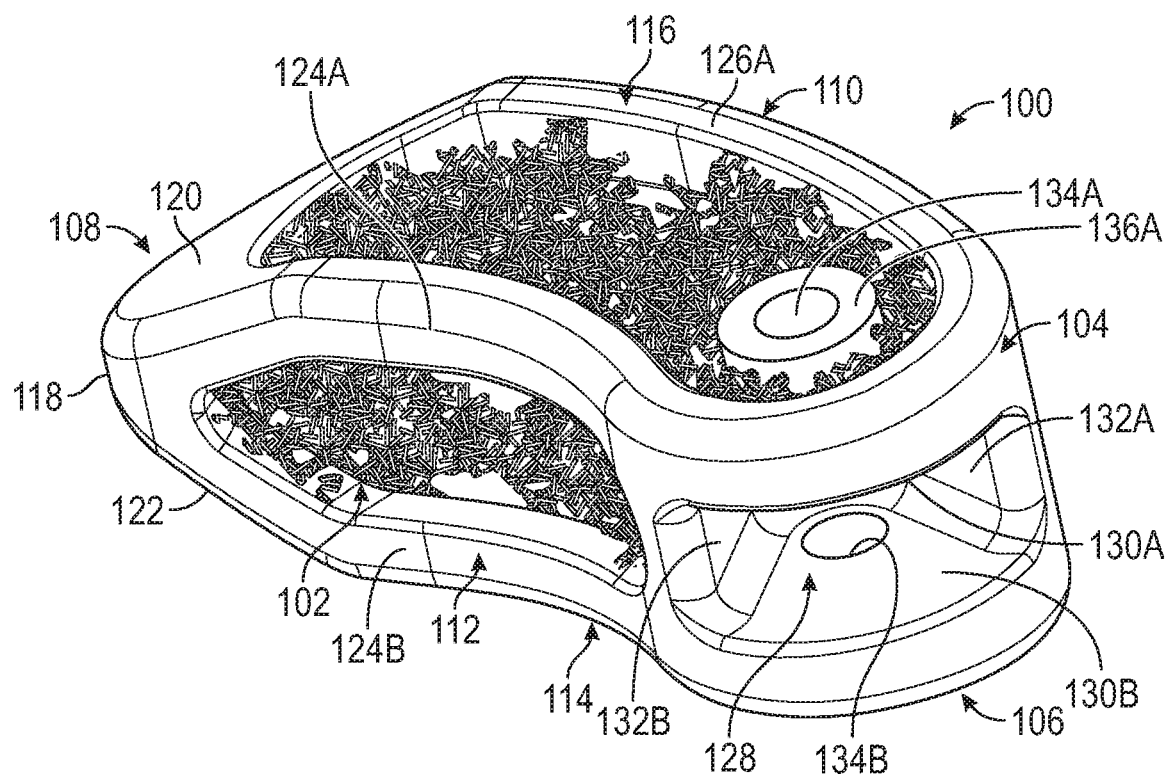
FIG. 14
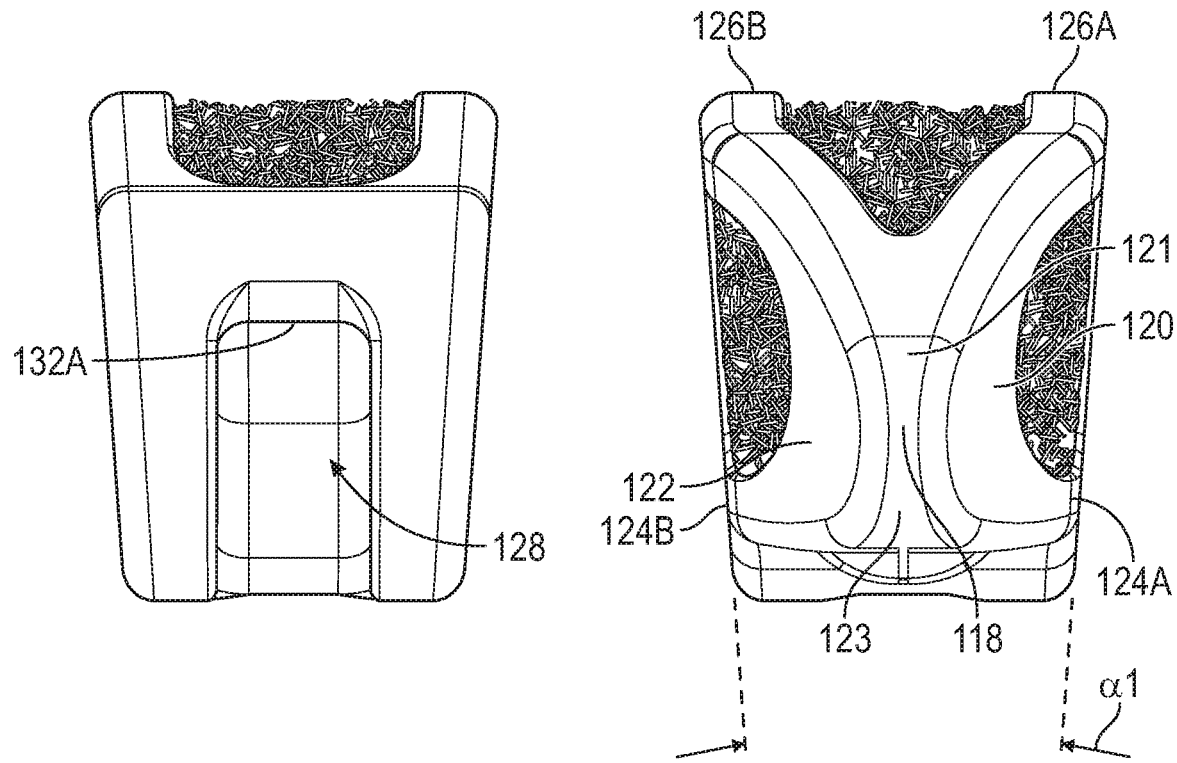
FIG. 15
FIG. 16

INTERVERTEBRAL IMPLANTS

CLAIM OF PRIORITY

This application claims the benefit of U.S. Provisional Patent Application Ser. No. 62/778,543, filed on Dec. 12, 2018, and claims the benefit of U.S. Provisional Patent Application Ser. No. 62/830,863, filed on Apr. 8, 2019, the benefit of priority of each of which is claimed hereby, and each of which is incorporated by reference herein in its entirety.

TECHNICAL FIELD

This document pertains generally, but not by way of limitation, to implants for positioning between adjacent bones, such as can be used in spinal correction procedures. More specifically, but not by way of limitation, the present application relates to implants having improved osseointegration.

BACKGROUND

A spinal column can require correction of spinal deformities and abnormalities resulting from trauma or degenerative issues. Various methods of correcting issues with the spinal column can include fusing adjacent vertebrae together with a spacer and/or a rod system to immobilize the degenerated portion of the spine. Such procedures can be beneficial in patients having diseased or degenerated disc material between the vertebrae. For example, intervertebral implants can be positioned between adjacent vertebrae to fuse the vertebrae together, after disk material located therebetween is removed. In order to facilitate fusion of the adjacent vertebrae, the implants can include various cavities and porous surfaces that promote growth of bone material into the implant. However, inclusion of such cavities and porous features can complicate construction of the implant and result in implants that are not as strong as is desirable for placement between adjacent vertebrae.

Examples of intervertebral spacer implants are described in U.S. Pat. No. 8,454,700 to Lemoine et al.; U.S. Pat. No. 9,662,226 to Wickham; and U.S. Pub. No. 2017/0333205 to Joly et al.

OVERVIEW

The present inventors have recognized, among other things, that a problem to be solved can include the difficulty of providing intervertebral implants that simultaneously provide bone support to the adjacent bones, facilitate in-growth of bone to enhance stability, that are easy to implant, and that better approximate the elastic modulus of natural bone. For example, it can be desirable to provide interbody implants that are porous to facilitate bone in-growth, but that are not too rigid such that they cannot compress under loading. Stiff implants can be both uncomfortable for the patient and can inhibit boney in-growth, as discussed below. Additionally, porous bodies can sometimes be difficult to implant between adjacent vertebrae due to the porous material catching on anatomy while being slid between the vertebrae.

Furthermore, the present inventors have recognized that intervertebral implants that are overly stiff in the superior-inferior direction can inhibit boney in-growth. For example, a rigid implant can be interpreted by the human body as being sufficiently strong if no compression occurs in the implant from adjacent vertebrae during movement of the spinal column. As such, the human body will not be induced into biologically promoting bone growth in that area. However, if the intervertebral implant is permitted to compress under loading from adjacent vertebrae during movement of the spinal column, the human body can interpret such compression as a need for strengthening the bones in that area and can therefore react by biologically promoting bone growth in those bones, which can subsequently extend into pores and cavities of an adjacent implant. The ideal intervertebral implant would perfectly mimic natural bone in order to enhance the natural healing reaction of surrounding tissues.

The present subject matter can help provide a solution to these problems, such as by providing an interbody implant that is porous to accept boney in-growth, while also not being overly stiff in the superior-inferior direction. The interbody implant can have a porous structure that has a stiffness (e.g., modulus of elasticity) that replicates stiffness of natural bone. The interbody implant can additionally be strengthened in other dimensions, such as in the transverse plane, to increase stability of the device and facilitate insertion into the anatomy. In particular, an interbody implant can have a porous structure being made of a material that has a stiffness that permits superior-inferior compression, but that is wrapped or partially surrounded along anterior, posterior and medial-lateral surfaces by a solid cage-like or cerclage structure to provide strength to the porous structure. The cage-like or cerclage structure can be smooth and shaped to facilitate insertion between vertebrae.

In an example, an interbody implant can comprise a first cage comprising an anterior segment, a medial segment, a posterior segment and a lateral segment contiguously connected to each other to define an interior space, and a porous structure located in the interior space and bounded by the cage and that can comprise opposed superior and inferior surfaces exposed through the first cage, an internal cavity located in an interior of the porous structure, and a plurality of ports connecting the internal cavity to the superior and inferior surfaces.

In another example, a method of implanting an interbody implant between adjacent bones to promote bone in-growth can comprise inserting the interbody implant between adjacent bones, the interbody implant can comprise a porous structure comprising a monolithic body formed of a porous material replicating porosity of human bone, an interior cavity, and a plurality of openings in the monolithic body extending from the interior cavity to an exterior of the monolithic body, and a cage structure circumscribing a portion of the monolithic body in a transverse plane, positioning the plurality of openings against surfaces of the bones to allow for in-growth, and permitting the porous structure to compress in a superior-inferior direction between the bones and within the cage structure to stimulate biological bone growth within the bones.

In an additional example, an intervertebral implant for lateral insertion can comprise a porous structure formed of a porous material that can be shaped to define an interior cavity and a plurality of longitudinal passages extending through the porous structure to intersect the internal cavity, a first cerclage cage horizontally surrounding the porous structure, and a second cerclage cage horizontally surrounding the porous structure uncoupled from the first cerclage cage such that a longitudinal stiffness of the intervertebral implant is defined by the porous structure.

While depicted in certain examples as being separate structures, the cage-like solid structures and the porous inner structure can be formed as a unitary structure, such as through additive manufacturing techniques including 3D printing using selective laser sintering, among others. Accordingly, despite being discussed and illustrated as separate structures, in certain examples the entire intervertebral implant can be 3D printed as a single structure with varying degrees of porosity.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 14 is a perspective view of a Transforaminal Lumbar Interbody Fusion (TLIF) device.

FIG. 15 is a handle-end view of the TLIF device of FIG. 14.

FIG. 16 is an insertion-end view of the TLIF device of FIG. 14.

Figure 1:
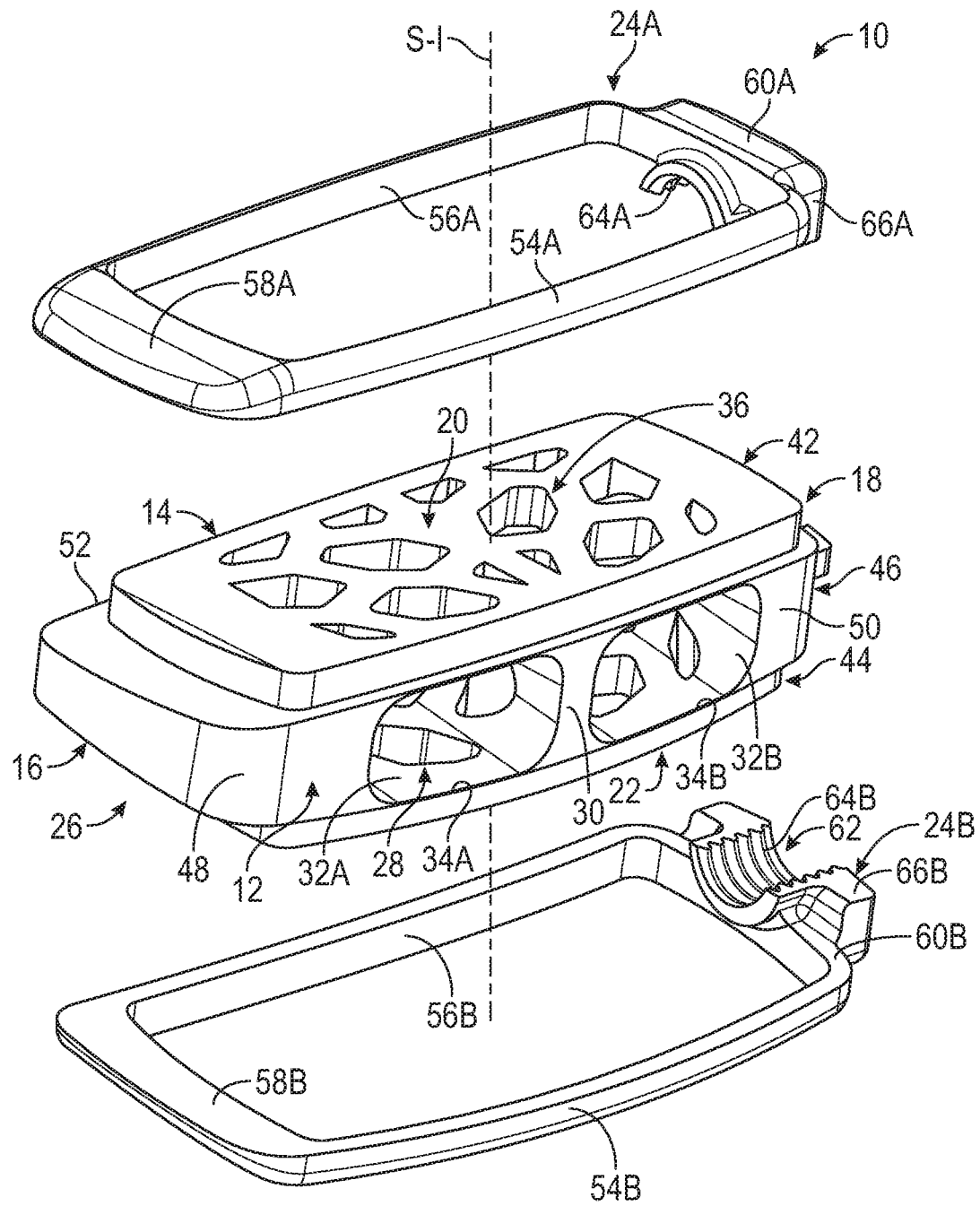
FIG. 1 is an exploded perspective view of an interbody implant of the present application showing the porous structure positioned between superior and inferior cages.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 2:
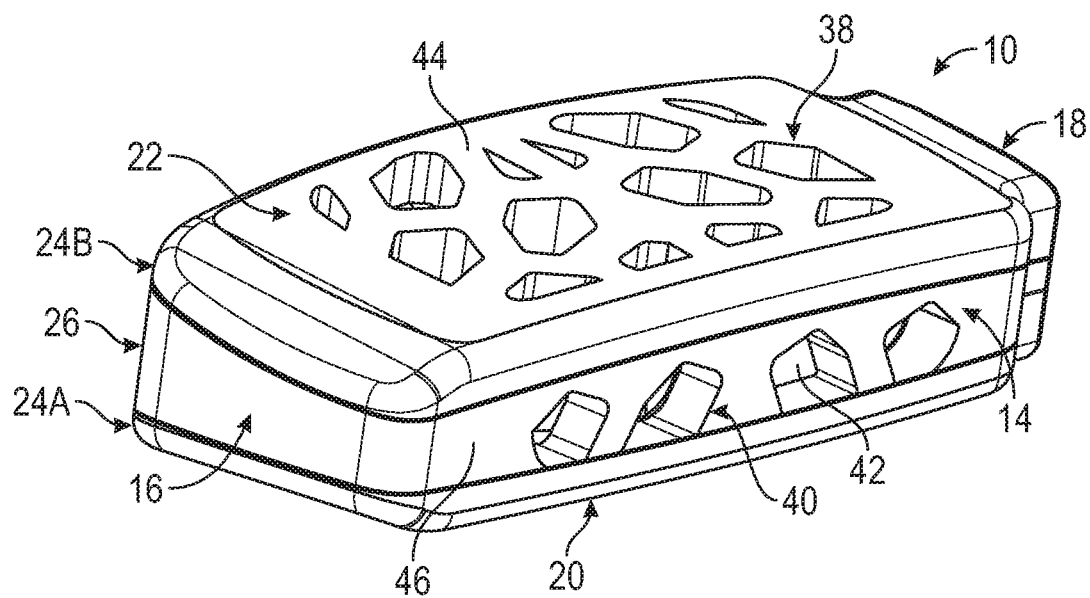
FIG. 2 is a perspective view of a posterior side of an interbody implant of FIG. 1 comprising a cage structure surrounding a porous structure.
Figure 3:
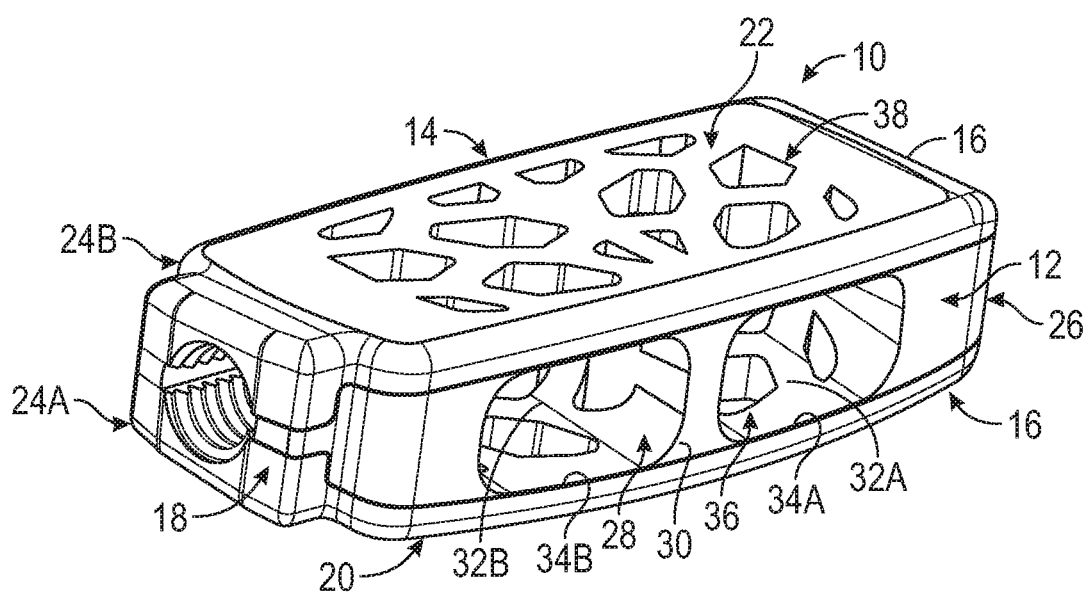
FIG. 3 is a perspective view of an anterior side of the interbody implant of FIGS. 1 and 2 showing an opening into an internal cavity of the porous structure.

FIG. 1 is an exploded perspective view of interbody implant 10 of the present application showing superior cage 24A, inferior cage 24B and porous structure 26. FIG. 2 is a perspective view of a posterior side of interbody implant 10 of FIG. 1. FIG. 3 is a perspective view of an anterior side of interbody implant 10 of FIGS. 1 and 2. FIGS. 1-3 are discussed concurrently.

Interbody implant 10 can comprise anterior surface 12, posterior surface 14, insertion surface 16, coupling surface 18, superior surface 20 and inferior surface 22. With reference to FIGS. 1-9, the present application shows and describes a particular orientation of interbody implant 10. However, other orientations can be used. For example, superior surface 20 and inferior surface 22 can be reversed such that coupling surface 18 and insertion surface 16 can be on either the medial or lateral side of the spinal column; e.g., interbody implant 10 can be rotated one-hundred-eighty degrees in the plane of FIG. 4. Likewise, anterior surface 12 can be used oriented toward a posterior of the patient e.g., interbody implant 10 can be rotated one-hundred-eighty degrees in the plane of FIG. 7.

Surfaces 12-22 can be defined, at least partially, by superior cage 24A, inferior cage 24B and porous structure 26. Porous structure 26 can define internal cavity 28, which can be divided by support wall 30 to form cavities 32A and 32B. In certain examples, internal cavity 28 can span a majority of the width of interbody implant 10, such as by eliminating support wall 30. Anterior surface 12 can comprise openings 34A and 34B into internal cavity 28. Superior surface 20 can include lattice structure 36, inferior surface 22 can include lattice structure 38 and posterior surface 14 can include lattice structure 40.

Interbody implant 10 can be shaped for positioning between adjacent anatomic bodies, such as adjacent vertebrae in a spinal column. Interbody implant can be configured to occupy space where a degenerative or damaged disk has been removed. As such, interbody implant 10 can be configured to directly contact bone, particularly at superior surface 20 and inferior surface 22. For example, superior surface 20 can contact the inferior surface of an upper vertebra and inferior surface 22 can contact the superior surface of a lower vertebra. Interbody implant 10 can be configured to promote bone in-growth into the surfaces of interbody implant 10 by inclusion of macro and micro pore structures. Porous structure 26 can include micro-pores by being made or fabricated from porous material, such as Trabecular Metal™ or OsseoTi™, that can include pores on the scale of natural bone porosity, for example. The material of porous structure 26 can additionally be shaped so that porous structure 26 includes macro-pores, such as can be formed by lattice structures 36, 38 and 40. Additionally, porous structure 26 can include internal cavity 28, which can provide a space for holding bone graft or other bone-growth-promoting materials to further promote in-growth of bone from the adjacent vertebrae.

In order to strengthen porous structure 26 to better withstand forces applied to interbody implant 10 when implanted between the adjacent vertebra, such as from bending and twisting of the spinal column, interbody implant 10 can be provided with one or both of cages 24A and 24B. Superior cage 24A can extend around interbody implant 10 along edges where superior surface 20 joins anterior surface 12, posterior surface 14, insertion surface 16 and coupling surface 18. Inferior cage 24B can extend around interbody implant 10 along edges where inferior surface 22 joins anterior surface 12, posterior surface 14, insertion surface 16 and coupling surface 18. Cages 24A and 24B can be curved or rounded, such as along a circular arc length in cross-section, to reduce or eliminate sharp edges. Cages 24A and 24B can be shaped and positioned to support porous structure 26, while also permitting interbody implant 10 to retain the properties of porous structure 26, particularly the stiffness, resiliency and modulus of elasticity characteristics of porous structure 26, such as in the superior-inferior S-I direction. In embodiments, cages 24A and 24B can comprise cerclage structures that circumscribe porous structure 26 in transverse planes, but do not contact each other in the superior-inferior direction. Thus, as discussed herein, interbody implant 10 can deform or compress in the superior-inferior direction according to the mechanical properties of porous structure 26, thereby simulating biological bone-growth conditions in adjacent vertebrae.

In examples, porous structure 26 and cages 24A and 24B can be made of separate pieces that are attached together. For example, cages 24A and 24B can be snap-fit onto porous structure 26, welded to porous structure 26 or attached via an adhesive. In other examples, porous structure 26 and cages 24A and 24B can be a monolithic structure. For example, porous structure 26 and cages 24A and 24B can be made as a single, monolithic structure using additive manufacturing processes.

With reference to FIG. 3, porous structure 26 can comprise superior panel 42, inferior panel 44 and middle panel 46. Middle panel 46 can comprise insertion side portion 48, coupler side portion 50, posterior portion 52 and support wall 30. Panels 42, 44 and 46 can be formed from the same piece of material so as to form a single, unitary, monolithic body. As discussed below with respect to FIG. 10, porous structure 26 can be formed by three-dimensional printing processes, a chemical vapor deposition process, and other procedures.

Superior cage 24A can comprise anterior leg 54A, posterior leg 56A, insertion leg 58A and coupler leg 60A. Inferior cage 24B can comprise anterior leg 54B, posterior leg 56B, insertion leg 58B and coupler leg 60B. Legs 54A-60A can be configured to surround superior panel 42. Legs 54B-60B can be configured to surround inferior panel 44. As such, the inner perimeters of superior cage 24A and inferior cage 24B can match the outer perimeters of superior panel 42 and inferior panel 44, respectively. The outer perimeters of superior cage 24A and inferior cage 24B can match the outer perimeter of middle panel 46. The superior-inferior height or thickness of superior cage 24A and inferior cage 24B can match the superior-inferior height or thickness of superior panel 42 and inferior panel 44, respectively. Interior portions of legs 54A-60B can include planar surfaces for engaging flush with panels 42, 44 and 46, respectively. Exterior portions of legs 54A-60B can include curved surfaces to facilitate sliding against tissue. When positioned around panels 42 and 44, cages 24A and 24B can provide strength to porous structure 26 to, for example, prevent expansion of the material of porous structure 26 in the transverse plane, which can protect the structural integrity of lattice structures 36 and 38, for example.

As discussed below with reference to FIG. 6, coupler legs 60A and 60B can form portions of a socket for coupling to a tool, such as a threaded socket for coupling with a shaft of an insertion tool. As discussed below with reference to FIG. 9, insertion legs 58A and 58B can be shaped to facilitate sliding of implant 10 between bodies such as adjacent vertebrae.

Figure 4:
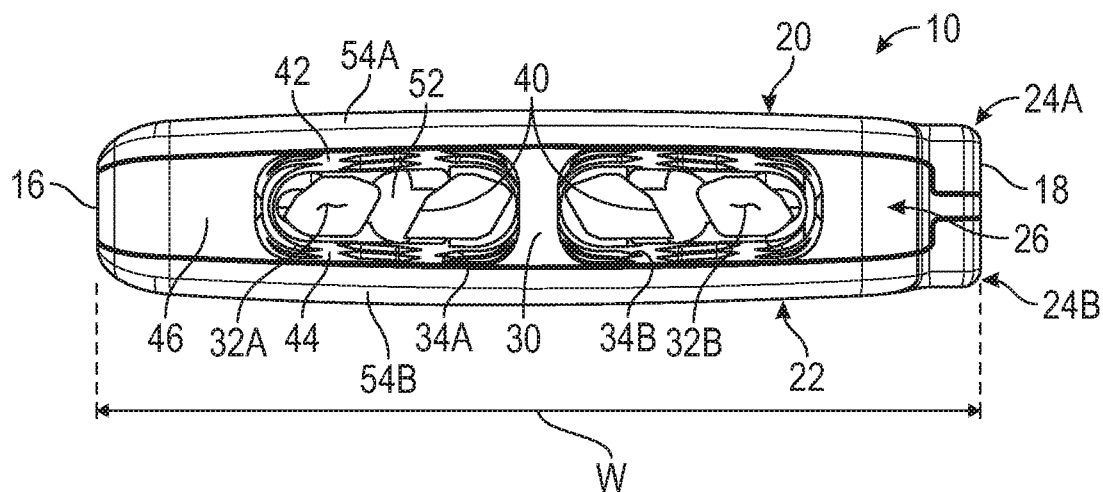
FIG. 4 is a plan view of the anterior side of the interbody implant of FIG. 1 showing a divider located in the internal cavity.
Figure 5:
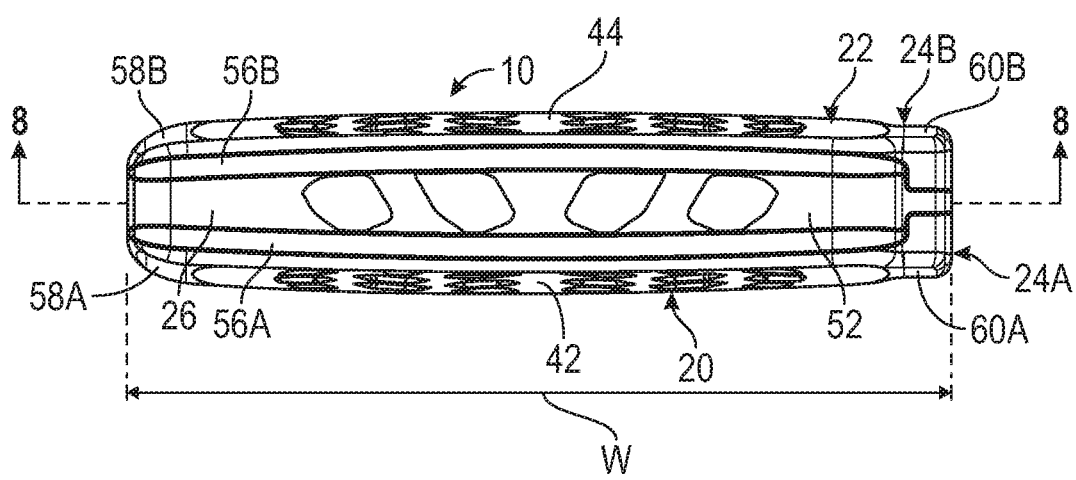
FIG. 5 is a plan view of the posterior side of the interbody implant of FIG. 2 showing a posterior surface including a lattice structure.

FIG. 4 is a plan view of the anterior side of interbody implant 10 of FIGS. 1-3 showing divider 30 located between openings 34A and 34B to internal cavity 28 of porous structure 26. FIG. 5 is a plan view of the posterior side of interbody implant 10 of FIGS. 1-3 showing posterior surface 14 including lattice structure 40. FIGS. 4 and 5 are discussed concurrently.

Anterior surface 12 of implant 10 can be formed by a lower portion of leg 54A of superior cage 24A, an upper portion of leg 54B of inferior cage 24B and an anterior surface of porous structure 26. Posterior surface 14 of implant 10 can be formed by a lower portion of leg 56A of superior cage 24A, an upper portion of leg 56B of inferior cage 24B and a posterior surface of porous structure 26. Surfaces 16 and 18 can be formed by lower portions of legs 58A and 60A of superior cage 24A, respectively, upper portions of legs 58B and 60B of inferior cage 24B, respectively, and medial-lateral surfaces of porous structure 26. Cages 24A and 24B can be uncoupled in the superior-inferior direction and can thus be separated by a distance comprising a portion of the thickness of porous structure 26. As such, downward or inferior pressure on implant 10 will permit porous structure 26 to deform or compress without interference from cages 24A and 24B.

Openings 34A and 34B can extend into the anterior surface of porous structure 26 between cages 24A and 24B. In examples, the superior-inferior height of openings 34A and 34B can be approximately equal to the superior-inferior distance between changes 24A and 24B. Support wall 30 can be positioned between openings 34A and 34B. Interbody implant 10 can have a medial-lateral width W. In examples, support wall 30 can be positioned at a medial-lateral center of interbody implant 10. Cavities 32A and 32B can extend from openings 34A and 34B to posterior portion 52 of middle panel 46 of porous structure 26. As such, an anterior-posterior path through interbody implant 10 can be formed by cavities 32A and 32B and lattice structure 40. As discussed in greater detail below with respect to FIGS. 7 and 8, lattice structure 40 can comprise a plurality of openings within posterior portion 52 extending from internal cavity 28 to the exterior of interbody implant 10. Openings 24A and 24B provide access to internal cavity 28 for the placement of bone graft material, bone cement or the like.

Figure 6:
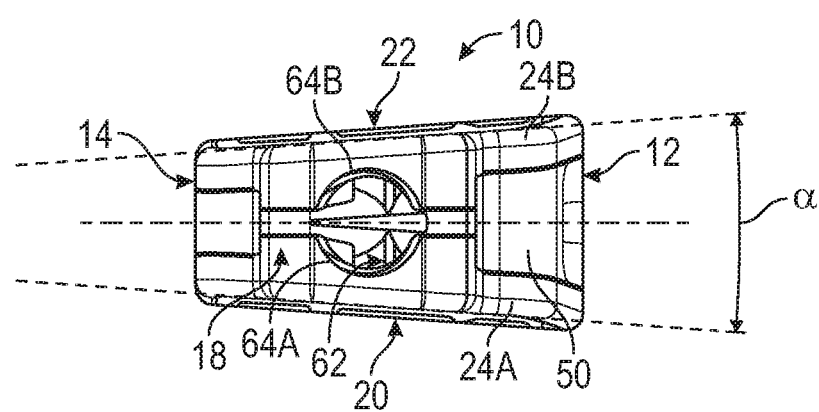
FIG. 6 is a plan view of a medial-lateral side of the interbody implant of FIG. 5 showing a coupler.

FIG. 6 is a plan view of a medial-lateral side of interbody implant 10 of FIGS. 1-3 comprising coupling surface 18. Coupling surface 18 can comprise socket 62, which can be defined by superior cage 24A and inferior cage 24B. Superior surface 20 and inferior surface 22 can be disposed relative to each other at angle α. The angle α can facilitate for interbody implant 10 inducing lordosis in the lumbar spine when implanted between lumbar vertebral bodies.

Figure 7:
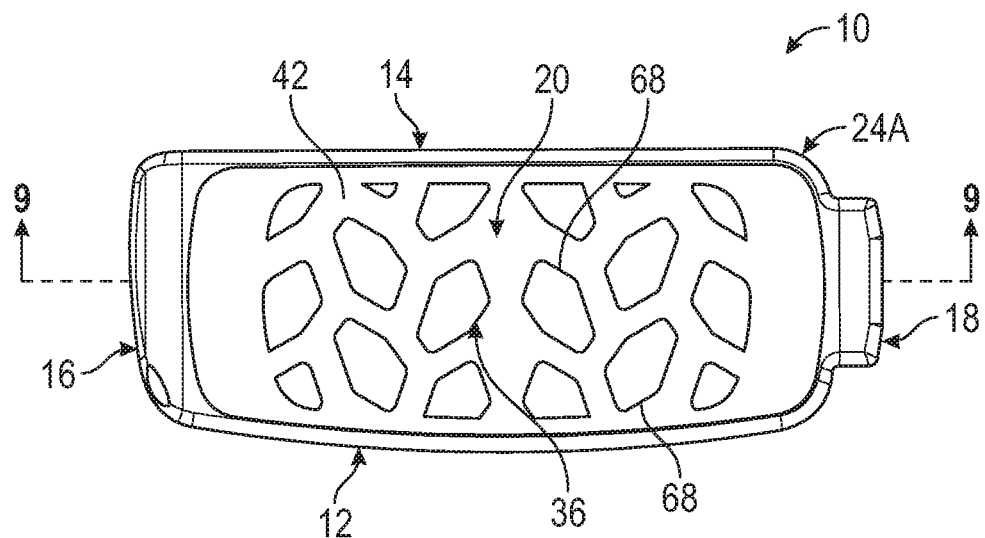
FIG. 7 is a plan view of a superior-inferior side of the interbody implant of FIG. 4 showing superior-inferior alignment of lattice structures in the porous structure.
Figure 8:
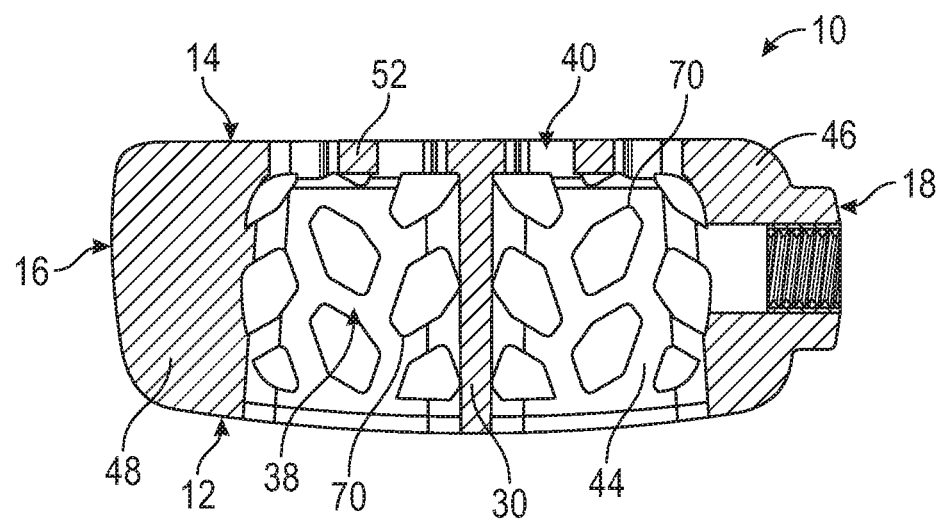
FIG. 8 is a cross-sectional view of the interbody implant taken at section 8-8 of FIG. 5 showing a shape of the internal cavity.

Socket 62 can be defined by superior segment 64A and inferior segment 64B. As mentioned, each of segments 64A and 64B can form portions of a socket for coupling to a tool, such as a threaded socket for coupling with a shaft of an insertion tool. As such segments 64A and 64B can comprise circular arc segments. In an example, each of segments 64A and 64B can form arc segments that are about one-hundred-sixty degrees. In various embodiments, each of segments 64A and 64B are less than one-hundred-eighty degrees and are centered upon a common center such that segments 64A and 64B do not contact each other. As shown in FIGS. 3, 7 and 8, segments 64A and 64B can be formed in legs 60A and 60B of cages 24A and 24B. As shown in FIG. 3, legs 60A and 60B can include flanges 66A and 66B, respectively, to provide axial (medial-lateral) length to segments 64A and 64B.

Figure 11:
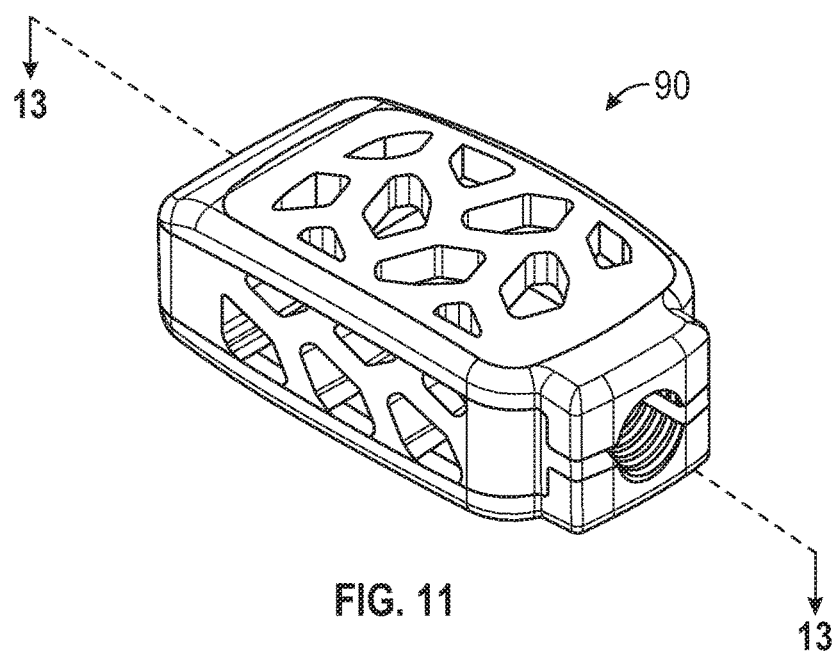
FIG. 11 is a perspective view of another embodiment of an interbody implant of the present application.
Figure 12:
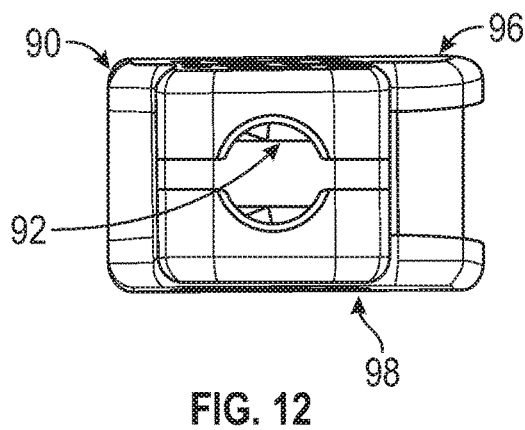
FIG. 12 is a plan view of a medial-lateral side of the interbody implant of FIG. 11 showing a coupler.
Figure 13:
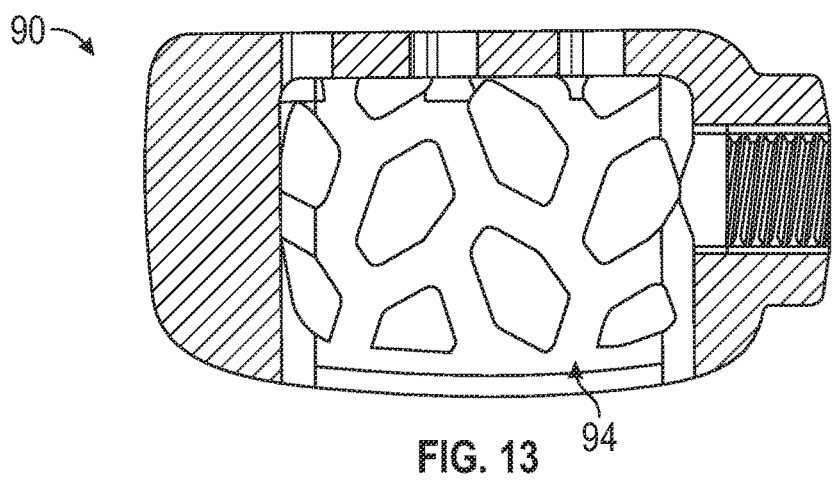
FIG. 13 is a cross-sectional view of the interbody implant taken at section 13-13 of FIG. 9 showing a shape of an internal cavity.

In different embodiments, the orientation between superior surface 20 and inferior surface 22 can be selected and set such that angle α can correspond to a desired wedge angle (e.g., lordosis) between adjacent vertebrae. For example, interbody implant 10 depicted in FIGS. 1-9 can be configured for use in the lower lumbar region of the spine between any of the L1-L5 vertebrae. In a particular example, interbody implant 10 can be used between the L4 and L5 vertebrae or the L5 and S1 vertebrae where the wedge angle can be in the range of about 6 degrees to about 10 degrees. However, in other embodiments, interbody implant 10 can be configured for use in other regions of a spinal column and can be configured such that superior surface 20 and inferior surface 22 are approximately parallel, such as is shown in FIG. 11-13. Furthermore, as discussed with reference to FIGS. 14-39, intervertebral implants according to the present disclosure can be configured for insertion into the spine at different levels and at different insertion approaches, e.g., anterior or posterior.

FIG. 7 is a plan view of a superior-inferior side of interbody implant 10 of FIGS. 1-3 comprising inferior surface 22 showing superior-inferior alignment of lattice structure 38 in inferior panel 44 of in porous structure 26 with lattice structure 36 (not visible in FIG. 7) in superior panel 42 (not visible in FIG. 7) of porous structure 26. FIG. 8 is a cross-sectional view of interbody implant 10 taken at section 8-8 of FIG. 5 showing a shape of internal cavity 28 and the location of lattice structure 36 in superior panel 42. FIGS. 7 and 8 are discussed concurrently.

As can be seen in FIG. 7, lattice structure 38 can align with lattice structure 36 in a superior-inferior direction such that edges of lattice structure 36 cannot be seen in porous structure 26. Alignment of lattice structures 36 and 38 can facilitate columnar growth of bone material through interbody implant 10, which can, for example, strengthen osseointegration of interbody implant 10 with the adjacent vertebrae.

Lattice structure 38 can comprise a plurality of openings 68 that can extend from internal cavity 28 to the exterior of porous structure 26. In examples, each of openings 68 can comprise a hexa-lobular structure having six sides, or a portion of such a hexa-lobular structure. In examples, each hexa-lobular structure can have sides with different lengths such that the hexa-lobular structures have an irregular shape. Such hexa-lobular structures can be advantageous in allowing bone growth through panels 42 and 44, while not compromising the structural integrity of panels 42 and 44. Lattice structure 36 can comprise a plurality of openings 70 that can extend from internal cavity 28 to the exterior of porous structure 26. In examples, each of openings 70 can be configured in the same matter as openings 68. Likewise, openings defining lattice structure 40 in posterior portion 52 can be configured similarly to openings 68.

As can be seen in FIG. 8, support wall 30 can have straight sidewalls that can extend parallel to an anterior-posterior axis extending through the center of interbody implant 10. As mentioned above, such a configuration can facilitate positioning, e.g., centering, of interbody implant between adjacent vertebrae. Furthermore, cavities 32A and 32B can form generally rectilinear, e.g., square, chambers within porous structure 26. However, cavities 32A and 32B can have any shape.

Figure 9:
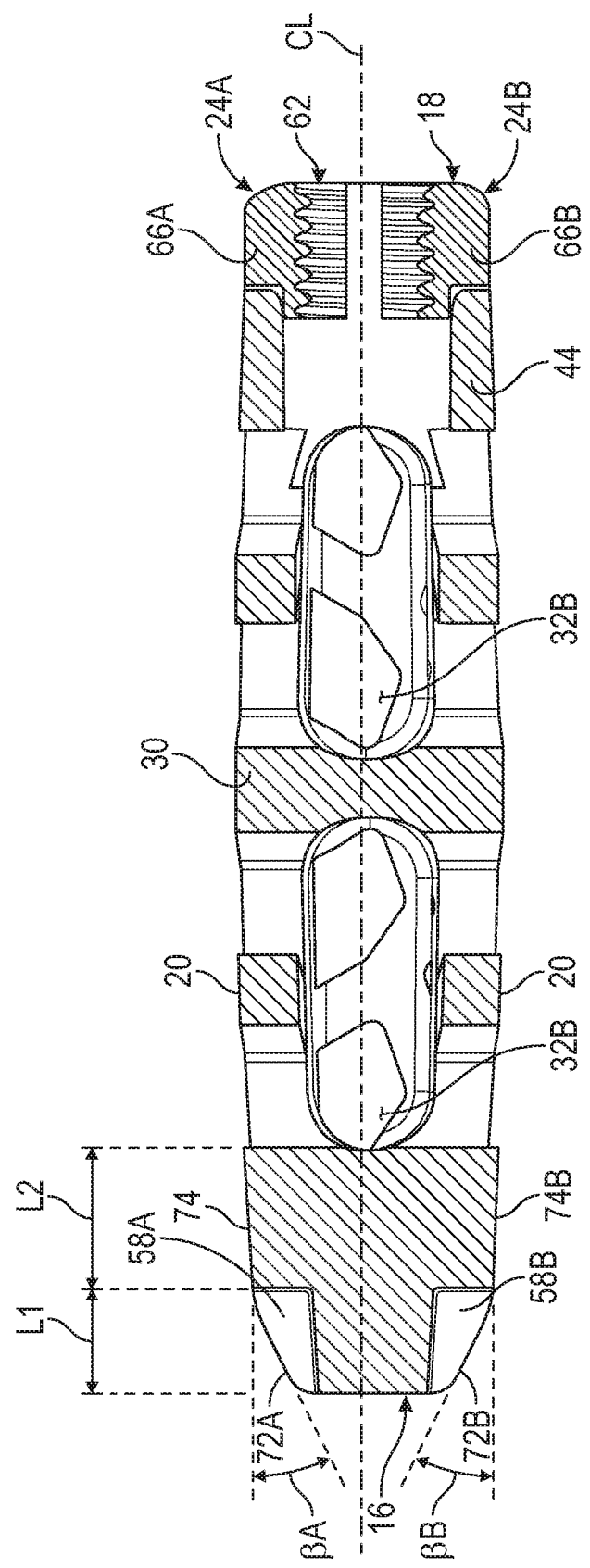
FIG. 9 is a cross-sectional view of the interbody implant taken at section 9-9 of FIG. 7 showing a wedge shape of a medial-lateral side of the interbody implant.

FIG. 9 is a cross-sectional view of interbody implant 10 taken at section 9-9 of FIG. 7 showing a wedge shape of a medial-lateral side of interbody implant 10 comprising insertion surface 16. Insertion surface 16 can be joined to superior surface 20 and inferior surface 22 by segments 72A and 72B. Segments 72A and 72B can comprise portions of legs 58A and 58B, respectively. Segments 72A and 72B can have flat exterior surfaces angled relative to centerline CL of interbody implant 10 at angles βA and βB. For example, segment 72A can be angled relative to centerline CL at angle βB. Angle βB can be in the range of approximately twenty to approximately forty degrees. Angle βA can be configured similarly to angle βB. Segments 72A and 72B can define the thinnest portion of the superior-inferior thickness of interbody implant 10. Segments 72A and 72B can include rounded exterior surfaces to smoothly blend segments 72A and 72B into superior surface 20, inferior surface 22 and coupling surface 18. The angling of segments 72A and 72B and the addition of curved edges can facilitate insertion of interbody implant 10 in between adjacent bodies, such as adjacent vertebrae. Segments 72A and 72B can thus provide the medial-lateral end of interbody implant 10 at coupling surface 18 with a wedge shape that can push tissue out of the way while interbody implant 10 is slid in between vertebrae. The wedge shape can additionally provide distraction to the adjacent vertebrae. Segments 72A and 72B can have a medial-lateral length L1 that can extend toward the medial-lateral middle of interbody implant 10 to provide a smooth surface for sliding against tissue. L1 can be greater than the thickness of legs 54A and 56A in the anterior-posterior direction, for example. Insertion side portion 48 can include superior segment 74A and inferior segment 74B that can extend length L2 from segments 72A and 72B, respectively. Superior segment 74A and inferior segment 74B, in addition to providing rigidity to porous structure 26, can form lengths of flat, porous surfaces that can extend from segments 72A and 72B to guide interbody implant against adjacent bones. That is, segments 74A and 74B can contact surfaces of adjacent bones to orientate interbody implant 10 in a horizontal position between the adjacent bones. Thus, segments 72A and 72B can clear tissue out of the way while segments 74A and 74B maintain the desired orientation of interbody implant to facilitate sliding. Segments 74A and 74B, while porous, do not include edges from lattice structures 36 and 38 and thereby can reduce snagging on tissue while also allowing bone in-growth after interbody implant 10 is fully implanted.

Figure 10:
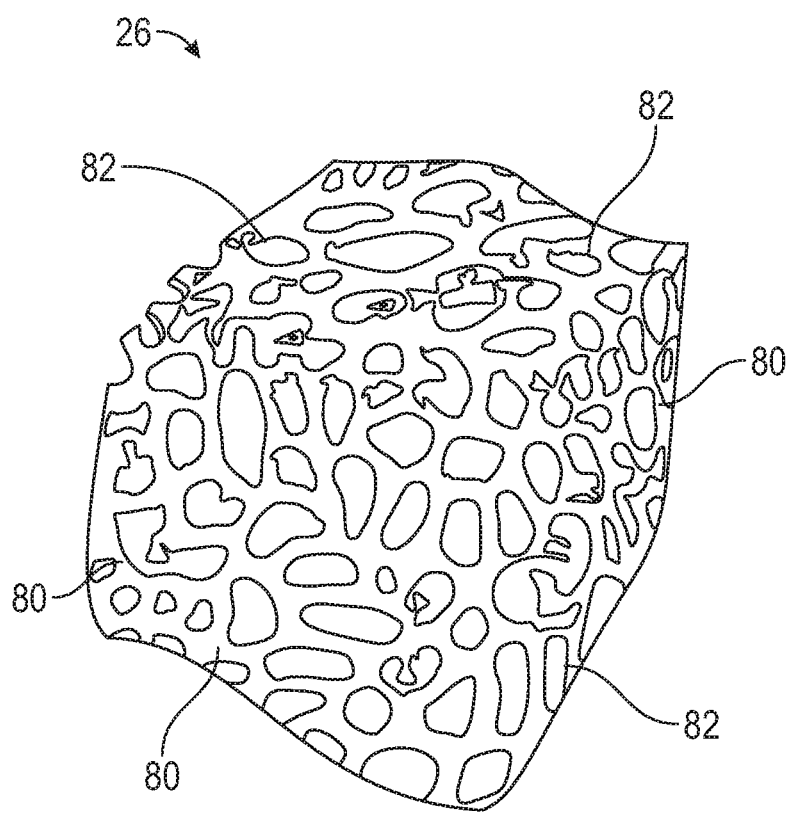
FIG. 10 is an exemplary perspective view of a portion of a porous structure of interbody implants of the present disclosure showing a plurality of interconnected endless ligaments forming a plurality of open spaces.

FIG. 10 is an exemplary perspective view of a portion of porous structure 26 of interbody implant 10 showing a plurality of interconnected endless ligaments 80 forming a plurality of open spaces 82.

Porous structure 26 can be formed of a suitable material that promotes bone in-growth and is biocompatible, such as porous metallic material, or a porous tantalum material. In examples, the porous material can have a porosity of approximately 20%-80% and pore sizes of approximately 50 μm-600 μm. An example of highly porous tantalum and titanium alloy materials is Trabecular Metal™ generally available from Zimmer Biomet, of Warsaw, Ind. Such a material may be formed from a reticulated vitreous carbon foam substrate which is infiltrated and coated with a biocompatible metal, such as tantalum, by a chemical vapor deposition (CVD) process in the manner disclosed in detail in U.S. Pat. No. 5,282,861 to Kaplan, the disclosure of which is expressly incorporated herein by reference in its entirety for all purposes. In addition to tantalum, other metals such as niobium, or alloys of tantalum and niobium with one another or with other metals may also be used.

In additional exemplary implementations, the porous metal structure can be a formed from a titanium alloy using an additive manufacturing process, such as with OsseoTi™, which is commercially available from Zimmer Biomet, of Warsaw, Ind. Briefly, OsseoTi is highly biocompatible, has high corrosion resistance and includes a highly interconnected porous architecture that mimics the porous structure of human cancellous bone, which can enhance bone integration and in-growth. In one exemplary implementation, the OsseoTi porous metal construct can include a porosity of 70%. OsseoTi™ material can be formed using a three-dimensional model of cancellous bone material as a template. The template can then be utilized to form any three-dimensionally printable structure, such as the porous structure of interbody implant 10 discussed herein.

In examples, porous structure 26 can be provided by any number of suitable three-dimensional, porous structures, and these structures can be formed with one or more of a variety of materials including but not limited to polymeric materials which are subsequently pyrolyzed, metals, metal alloys, ceramics. In some instances, a highly porous three-dimensional structure will be fabricated using a selective laser sintering (SLS) or other additive manufacturing-type process such as direct metal laser sintering. In one example, a three-dimensional porous article is produced in layer-wise fashion from a laser-fusible powder, e.g., a polymeric material powder or a metal powder, that is deposited one layer at a time. The powder is fused, remelted or sintered, by the application of laser energy, or energy from another source, that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain embodiments, a laser selectively fuses powdered material by scanning cross-sections generated from a 3-D digital description of the article, e.g., from a CAD file or scan data, on the surface of a powder bed. Net shape and near net shape constructs are infiltrated and coated in some instances. Unfused material can be removed from the completed component. Other types of rapid manufacturing processes can be used to fabricate the interbody implant, such as 3D printing processes.

Complex geometries can be created using such techniques. In some instances, a three-dimensional porous structure will be particularly suited for contacting bone and/or soft tissue, and in this regard, can be useful as a bone substitute and as cell and tissue receptive material, for example, by allowing tissue to grow into the porous structure over time to enhance fixation (i.e., osseointegration) between the structure and surrounding bodily structures, for example, to provide a matrix approximating natural cancellous bone or other bony structures. In this regard, a three-dimensional porous structure, or any region thereof, may be fabricated to virtually any desired density, porosity, pore shape, and pore size (e.g., pore diameter). Such structures therefore can be isotropic or anisotropic.

Such structures can be infiltrated and coated with one or more coating materials. When coated with one or more biocompatible metals, any suitable metal may be used including any of those disclosed herein such as tantalum, titanium, a titanium alloy, cobalt chromium, cobalt chromium molybdenum, tantalum, a tantalum alloy, niobium, or alloys of tantalum and niobium with one another or with other metals. In various examples, a three-dimensional porous structure may be fabricated to have a substantial porosity, density, pore shape and/or void (pore) size throughout, or to comprise at least one of pore shape, pore size, porosity, and/or density being varied within the structure. For example, a three-dimensional porous structure to be infiltrated and coated may have a different pore shape, pore size and/or porosity at different regions, layers, and surfaces of the structure.

In some embodiments, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as titanium, a titanium alloy, cobalt chromium, cobalt chromium molybdenum, tantalum, or a tantalum alloy. In some examples, cages 24A and 24B can form a support structure when building (printing) porous structure 26.

The rapid manufacturing processes can be used to include a desired level of porosity directly into porous structure 26. Likewise, lattice structures 36, 38 and 40 can be made to have any desired shape, size, number and aggregate strength and density in order to generate sufficient bonding strength to survive implantation and operation of porous structure 26, while permitting infusion of bone from lattice structures 36, 38 and 40, as described herein. In examples, the size of the macro-pores described herein can be sized to the overall size of the porous structure. For example, the size of macro-pores 2323A-232F can be scaled to the overall footprint of porous structure 202. Likewise, the overall cross-sectional surface areas of the various devices can be scaled as the height of the devices increases. For example, the size of pocket 236 can increase as the height of porous structure 202 increases.

The porous structures described herein can have sufficient strength to support the weight of and forces generated by a spinal column. However, the greater the porosity of the structures, such as the larger that internal cavity 28 is or the larger the total volume of lattice structures 36, 38 and 40 are, the weaker the porous structure becomes. Thus, in a static environment, porous structure 26 is sufficiently strong to support a spine. However, repeated compression and wear from movement of the spine can, in some circumstances, generate stress within the porous structure, that, particularly in the transverse plane as material of the porous structure is compressed by the spine. Edges of the porous structure can particularly become stressed. As such, with the devices described herein, cages 24A and 24B can be provided and coupled to porous structure 26 to provide targeted strength to porous structure 26. It has been found that, due to the inherent strength of porous structure 26, not a lot of additional support is beneficial. As such, in embodiments, cages 24A and 24B can comprise only about 15% by volume of interbody implant 10 for the depicted embodiment of FIGS. 1-9. However, a greater or lesser volume can be used depending on where and how much additional strengthening is desired.

Interbody implant 10 can be implanted between adjacent bones, such as adjacent vertebrae, to promote bone ingrowth. A method of implanting interbody implant 10 can include properly preparing and performing a lateral incision in a patient to access a medial or lateral portion of a spine adjacent an area where damaged or diseased intervertebral tissue is located. Soft tissue can be retracted using appropriate instrumentation to provide better access to the damaged or diseased intervertebral tissue. The damaged or diseased intervertebral tissue can be removed using appropriate methods to clear access to inferior and superior bone surfaces of the adjacent vertebrae.

Bone-growth-promoting material can be packed into internal cavity 28. In various examples, bone-growth-promoting material can be packed into internal cavity 28 before implantation. However, in some embodiments described herein, bone-growth-promoting material can be packed after implantation, such as in transverse designs. Interbody implant 10 can be attached to a tool, such as by threading a shaft of an insertion instrument into socket 62. Interbody implant 10 can be manipulated by a surgeon, robot or another person to position insertion surface 16 in the incision. Interbody implant 10 can be oriented in a desired direction such that anterior surface 12 is pointed toward the anterior of the spine and posterior surface 14 is pointed toward the posterior of the spine. Segments 72A and 72B of cages 24A and 24B can be engaged with soft tissue that is located medially or laterally of the implantation site in the spine. The insertion tool can be pushed to slide soft tissue across segments 72A and 72B. The angling of segments 72A and 72B can push the soft tissue out of the way of interbody implant 10 to inhibit soft tissue from scraping along lattice structures 36 and 38. The insertion tool can be pushed until segments 72A and 72B engage the exposed superior and inferior bone surfaces of the adjacent vertebrae where disc material has been removed. Segments 72A and 72B can be pushed in between the adjacent vertebrae and can act as a wedge to help spread the vertebrae to receive the full thickness of interbody implant 10. Interbody implant 10 can continue to be pushed until lattice structures 36 and 38 are positioned adjacent the exposed superior and inferior bone surfaces of the adjacent vertebrae. Interbody implant 10 can be positioned such that support wall 30 is centered on the vertebrae. If deemed desirable by the surgeon to verify placement of interbody implant 10, a surgeon can obtain imaging of the patient so that the location of support wall 30 relative to the medial and lateral sides of the vertebrae can be viewed and measured. After interbody implant 10 is positioned, the insertion tool can be removed from interbody implant 10 and the incision in the patient can be appropriately closed to leave interbody implant 10 within the patient. The interbody implant 10 can be shaped for use in an anterior approach, a lateral approach, a transforaminal approach, or a posterior approach spinal fusion surgery. The examples illustrated herein are generally intended for lateral, transverse, posterior and anterior approaches.

With interbody implant 10 positioned between bone surfaces of the adjacent vertebrae, bone from the vertebrae can grow into the micro-pores of porous structure 26 and into the macro-pores formed by lattice structures 36, 38 and 40. The bone-growth-promoting material located within internal cavity 28 can interact with the vertebrae to enhance bone growth. Furthermore, movement of the vertebrae, such as by bending and twisting of the spine, can apply compression to interbody implant 10. Because cages 24A and 24B are uncoupled in the superior-inferior direction, compressive forces applied to interbody implant 10 in the superior-inferior direction by the spine can be transmitted directly to porous structure 26. Porous structure 26 can be configured to have mechanical properties that replicate natural bone, e.g., stiffness, resiliency and modulus of elasticity. Thus, as described herein compression of porous structure 26 can stimulate biological growth of bone at the vertebrae contacting interbody implant 10. As bone grows into interbody implant 10, the superior and inferior vertebrae can become fused together through interbody implant 10.

FIG. 11 is a perspective view of interbody implant 90 comprising another embodiment of an interbody implant of the present application. FIG. 12 is a plan view of a medial-lateral side of interbody implant 90 of FIG. 11 showing coupler 92. FIG. 13 is a cross-sectional view of interbody implant 90 taken at section 13-13 of FIG. 9 showing a shape of internal cavity 94.

Interbody implant 90 can be configured in a similar manner as interbody implant 10 except that interbody implant 90 can have a shorter medial-lateral width, support wall 30 can be omitted, and superior surface 96 and inferior surface 98 can be generally parallel to each other.

Interbody implant 90 can be configured for use in the thoracic region of the spine between any of the T1-T12 vertebrae. In a particular example, interbody implant 90 can be used between the T11 and T12 vertebrae. Dimensions of interbody implants described herein can be adjusted and changed for use between any vertebrae in any region of the spine, including the cervical region, thoracic region and lumbar region.

The systems, devices and methods discussed in the present application can be useful in manufacturing and implanting porous interbody implants, such as those that can be used in spinal correction procedures involving lateral, transverse, anterior or posterior insertion of a spacer between adjacent vertebrae. The interbody implant can have micro and macro porosity to accept growth of bone into the implant. The material of the interbody implant can inherently have a micro-porous structure and can be shaped into having a macro-porous structure, wherein pores of the micro-porous structure can be large enough to accept bone in-growth and pores of the macro-porous structure can be small enough to enable the device to support adjacent bone structures. The material can compress to biologically induce a human body into promoting bone growth in the implant region of the body. The material of the interbody implant can be strengthened by one or more cage-like or cerclage structures that facilitate cohesion of the interbody implant, such as in the transverse plane. The cage-like or cerclage structures can additionally be textured, e.g. to be smooth, and shaped, e.g., to include a wedge-shaped end, to facilitate insertion between vertebrae. The cage-like or cerclage structures can include superior and inferior portions that are uncoupled from each other to not interfere with superior-inferior compression of the material forming the micro and macro porous structure. However, in additional examples, the cage-like or cerclage structures can be directly coupled or attached to, for example, provide additional strength.

FIGS. 1-13 illustrate an intervertebral implant configured for lateral applications. FIGS. 14-39 illustrate other configurations of intervertebral implants that can be made according to the present disclosure for different insertion approaches and for various levels of the spine. Specifically, FIGS. 14-21 show a Transforaminal Lumbar Interbody Fusion (TLIF) device, FIGS. 22-29 show a Posterior Lumbar Interbody Fusion (PLIF) device, FIGS. 30-34 show an anatomic Anterior Cervical Interbody Fusion (ACIF) device, and FIGS. 35-39 show a lordotic Anterior Cervical Interbody Fusion (ACIF) device. Features of the various configurations described herein can be combined. Each configuration is suitable for producing a solid cerclage or cage-like structure that can surround and support a micro-porous structure that can be integrally produced, such as with additive manufacturing techniques, or separately produced. Each configuration is suitable for producing intervertebral implants having desired compression or modulus of elasticity properties. Though the porous structure may be depicted or illustrated as having a different appearance with respect to specific embodiments, the porous structures described herein can comprise any porous structure as described or referenced herein, such as with respect to FIG. 10.

FIG. 14 is a perspective view of Transforaminal Lumbar Interbody Fusion (TLIF) device 100 comprising porous structure 102 and cage 104. Cage 104 can comprise handle-end 106, insertion-end 108, anterior side 110 and posterior side 112. Bone-facing surfaces 114 and 116 can comprise superior or inferior surfaces. Cage 104 can comprise tip 118, first slide surface 120, second slide surface 122, posterior rails 124A and 124B, anterior rails 126A and 126B, and socket 128. Socket 128 can comprise transverse surfaces 130A and 130B, longitudinal surfaces 132A and 132B, first and second bores 134A and 134B, and first and second bosses 136A and 136B.

Superior wall 138 and inferior wall 142 can be disposed relative to each other at angle α1. The angle α1 can facilitate for interbody implant 100 inducing lordosis in the lumbar spine when implanted between lumbar vertebral bodies. In examples, angle α1 can be in the range of zero to thirty degrees. In the illustrated embodiment, angle α1 is approximately eight degrees.

Figure 19:
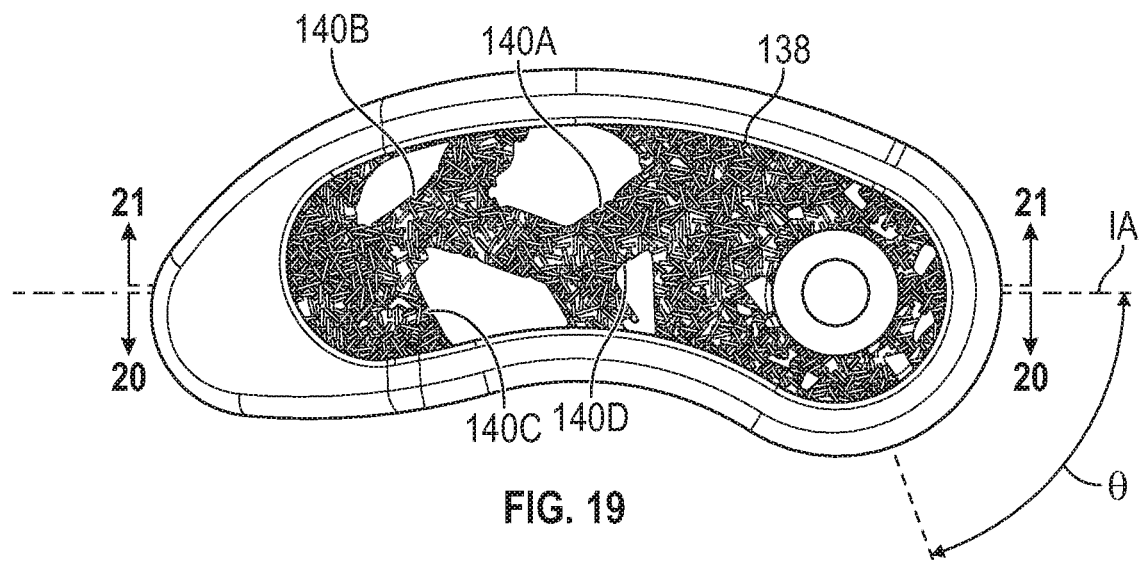
FIG. 19 is a superior view of the TLIF device of FIG. 14.

Slide surfaces 120 and 122, rails 124A-126B and socket 128 can form a cage-like structure as described herein for supporting porous structure 102, as described herein. Porous structure 102 can comprise superior wall 138, which, as shown in FIG. 19, can include macro-pores 140A, 140B, 140C and 140D. Macro-pores 140A-140D can extend down through inferior wall 142. Pocket 144 can be located between superior wall 138 and inferior wall 142. Superior wall 138 and inferior wall 142 can be connected by sidewalls 145A and 145B and anterior wall 146, which can include macro-pores 148A-148C. Additionally, pocket 144 can be provided with one or more support walls, such as support wall 30 of FIGS. 1 and 3.

Figure 17:
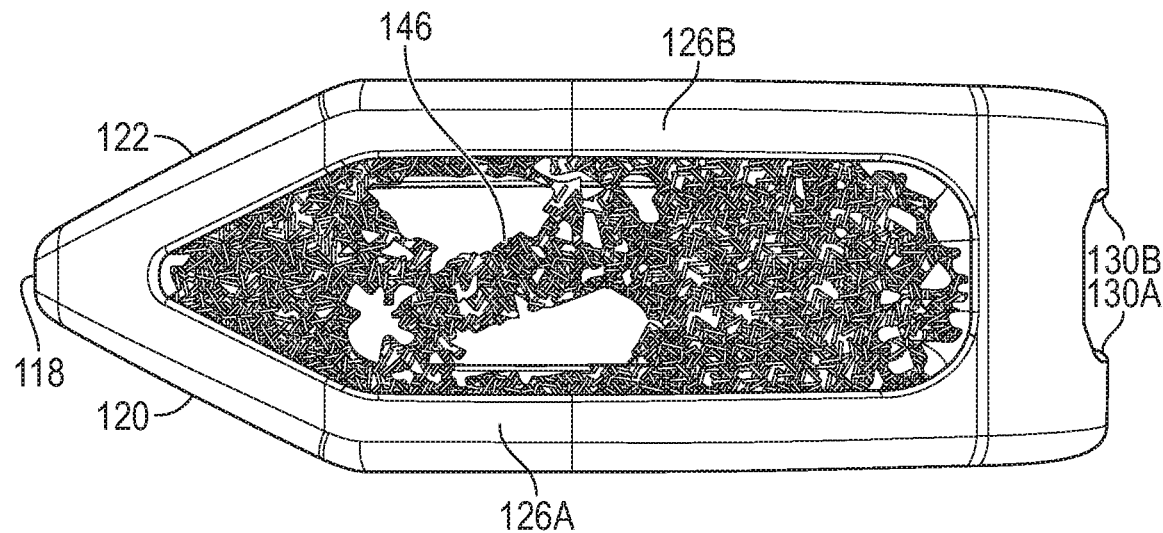
FIG. 17 is an anterior view of the TLIF device of FIG. 14.
Figure 18:
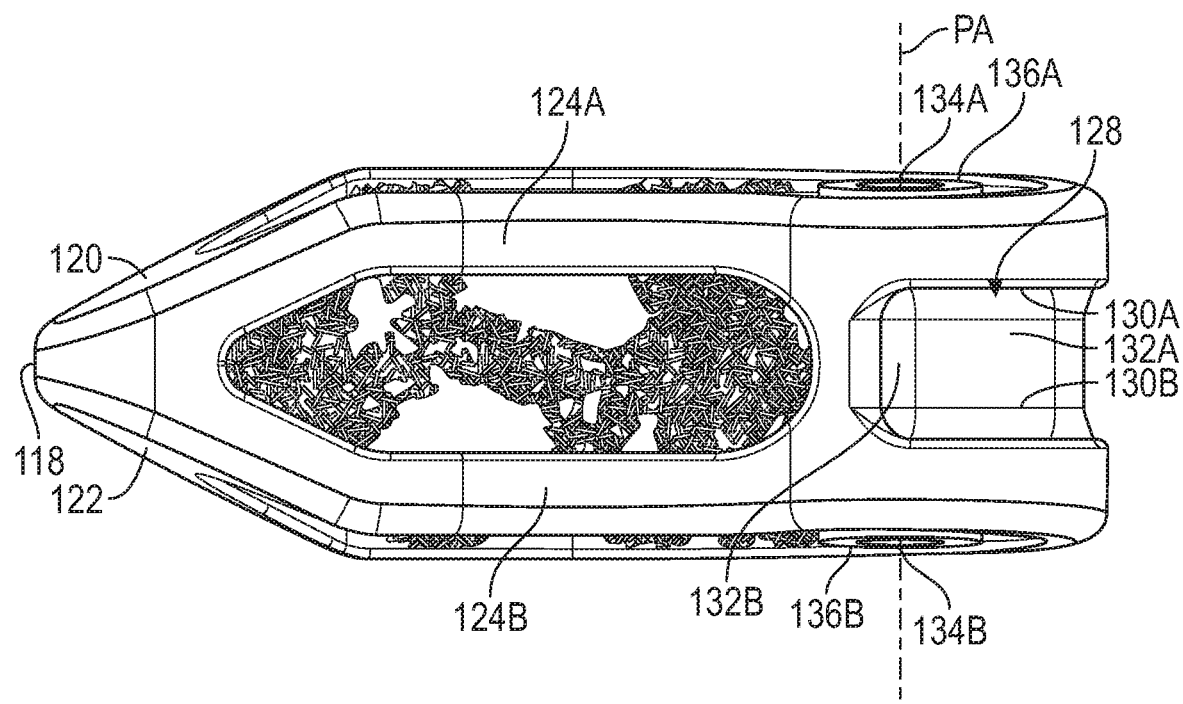
FIG. 18 is a posterior view of the TLIF device of FIG. 14.
Figure 20:
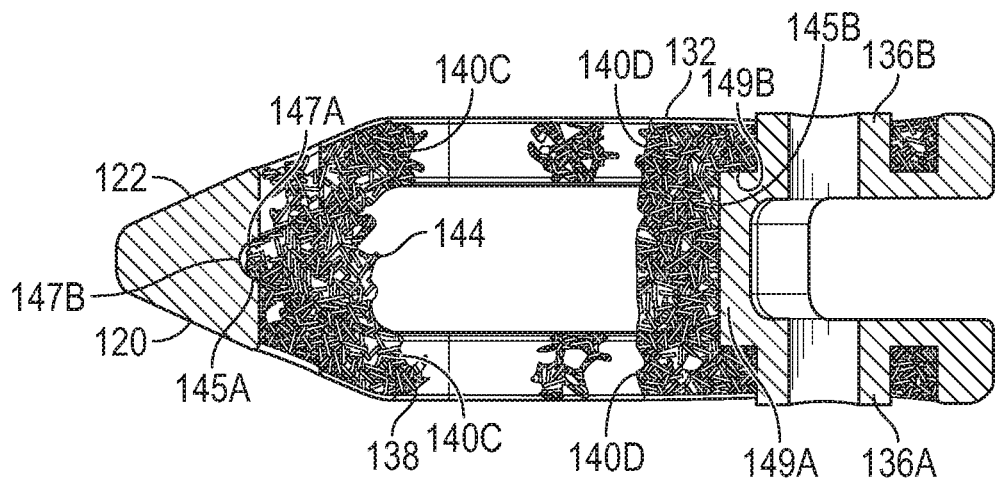
FIG. 20 is a cross-sectional view of the TLIF device of FIG. 19 taken at section 20-20 looking rearward.
Figure 21:
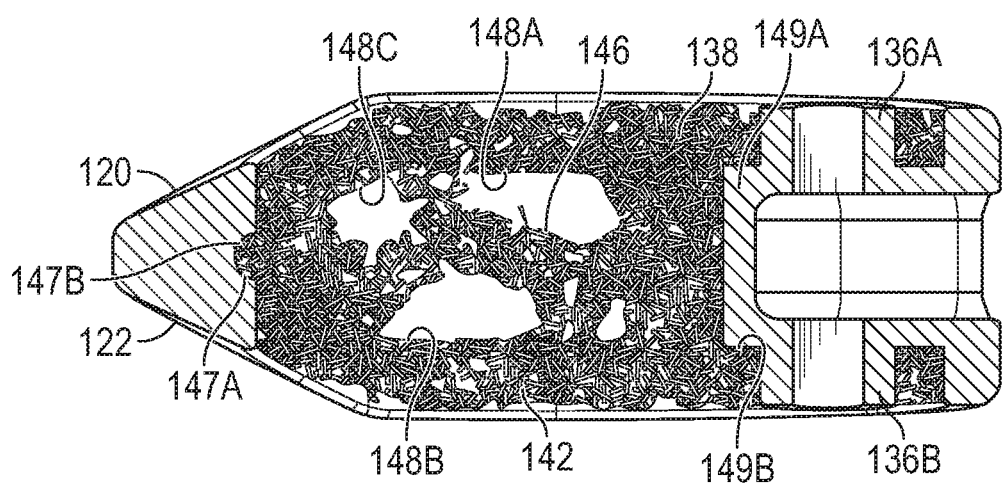
FIG. 21 is a cross-sectional view of the TLIF device of FIG. 19 taken at section 21-21 looking forward.

FIG. 15 is a handle-end view of TLIF device 100 of FIG. 14 showing socket 128. FIG. 16 is an insertion-end view of TLIF device 100 of FIG. 14 showing tip 118. FIG. 17 is an anterior view of TLIF device 100 of FIG. 14 showing anterior wall 146. FIG. 18 is a posterior view of TLIF device 100 of FIG. 14 showing socket 128. FIG. 19 is a superior view of TLIF device 100 of FIG. 14 showing superior wall 138. FIG. 20 is a cross-sectional view of TLIF device 100 of FIG. 19 taken at section 20-20 looking rearward to show pocket 144. FIG. 21 is a cross-sectional view of TLIF device 100 of FIG. 19 taken at section 21-21 looking forward to show anterior wall 146. FIGS. 14-21 are discussed concurrently and mentioned specifically where applicable.

Porous structure 102 can be open on posterior side 112 to allow placement of bone-growth material into porous structure 102 adjacent superior wall 138, inferior wall 142 and anterior wall 146. Thus, inferior wall 142, sidewall 145A, superior wall 138 and sidewall 145B can encircle the bone-growth material with anterior wall 146 inhibiting the bone-growth material from freely passing through porous structure 102. Furthermore, as shown in FIGS. 20 and 21, porous structure 102 can comprise bump 147A for residing in detent 147B in cage 104. Additionally, cage 104 can comprise bump 149A for residing in detent 149B in porous structure 102. Bumps 147A and 149A and detents 147B and 149B can be configured to assist in retaining porous structure 102 within cage 104, such as when porous structure 102 is not monolithic with cage 104.

First slide surface 120 and second slide surface 122 can be angled relative to bone-facing surfaces 114 and 116 and can be angled toward each other near tip 118. In examples, the angle between first slide surface 120 and second slide surface 122 can be in the range of 25 degrees to 80 degrees. Likewise, anterior side 110 and posterior side 112 can include slide surfaces 121 and 123 that can be curved to come together at tip 118. Tip 118 can be rounded to join anterior side 110 and posterior side 112. Tip 118 can separate slide surfaces 120 and 122. As such, tip 118 can pointed to provide an insertion tip for penetrating into and sliding past tissue, as described above. Rails 124A-126B can curved to conform with the geometry of vertebrae. In examples, anterior rails 126A and 126B can be curved in the posterior direction such that anterior side 110 is convex, and posterior rails 124A and 124B can be curved in the posterior direction such that posterior side 112 is concave. In examples, anterior side 110 and posterior side 112 can have a curvature that conforms with the anatomical curvature of the body portion of a vertebra. In examples, anterior side 110 and posterior side 112 can be curved to provide contact with cortical bone of the body portion of the vertebra.

Socket 128 can form a port for receiving a tool that can be coupled to TLIF device 100 for insertion of TLIF device 100 between vertebrae. Socket 128 can permit the tool to be variably positioned relative to cage 104 to facilitate insertion of TLIF device 100. A tool can be coupled to cage via insertion of a pin through bores 134A and 134B to articulate about pivot axis PA between longitudinal surfaces 132A and 132B. In examples, bores 134A and 134B can be threaded. Transverse surfaces 130A and 130B can engage the tool throughout the range of articulation to maintain cage 104 parallel to the tool. In examples, longitudinal surfaces 132A and 132B can be disposed at angle θ (FIG. 19) relative to each other. In examples, angle θ can be in the range of sixty to thirty degrees. In the illustrated embodiment, angle θ is approximately forty-five degrees. In an example, longitudinal surface 132B can be disposed parallel to insertion axis IA (FIG. 19). In an example, longitudinal surface 132B can be coincident with insertion axis IA (FIG. 19). In another configuration, longitudinal surfaces 132A and 132B can be made as part of porous structure 102 and tip 118 can include a slit or break so that rails 124A and 126A can be uncoupled from rails 124B and 126B.

TLIF device 100 is configured for insertion in between vertebrae from a posterior side of the spinal column. More specifically, TLIF device 100 is configured for insertion into a spinal column between a spinous process and an adjacent transverse process. TLIF device 100 can be configured, e.g., with different thicknesses, sized, widths, lengths to accommodate usage at different levels in the spinal column or in different sized patients. TLIF device 100 can be rotated on axis PA while being inserted to position TLIF device 100 to extend across the spinal column. An insertion device can be coupled to handle-end 106 and insertion-end 108 can be pushed through tissue into the spinal column such that bone-facing surfaces 114 and 116 align with an inferior surface of a superior vertebra and a superior surface of an inferior vertebra.

Figure 22:
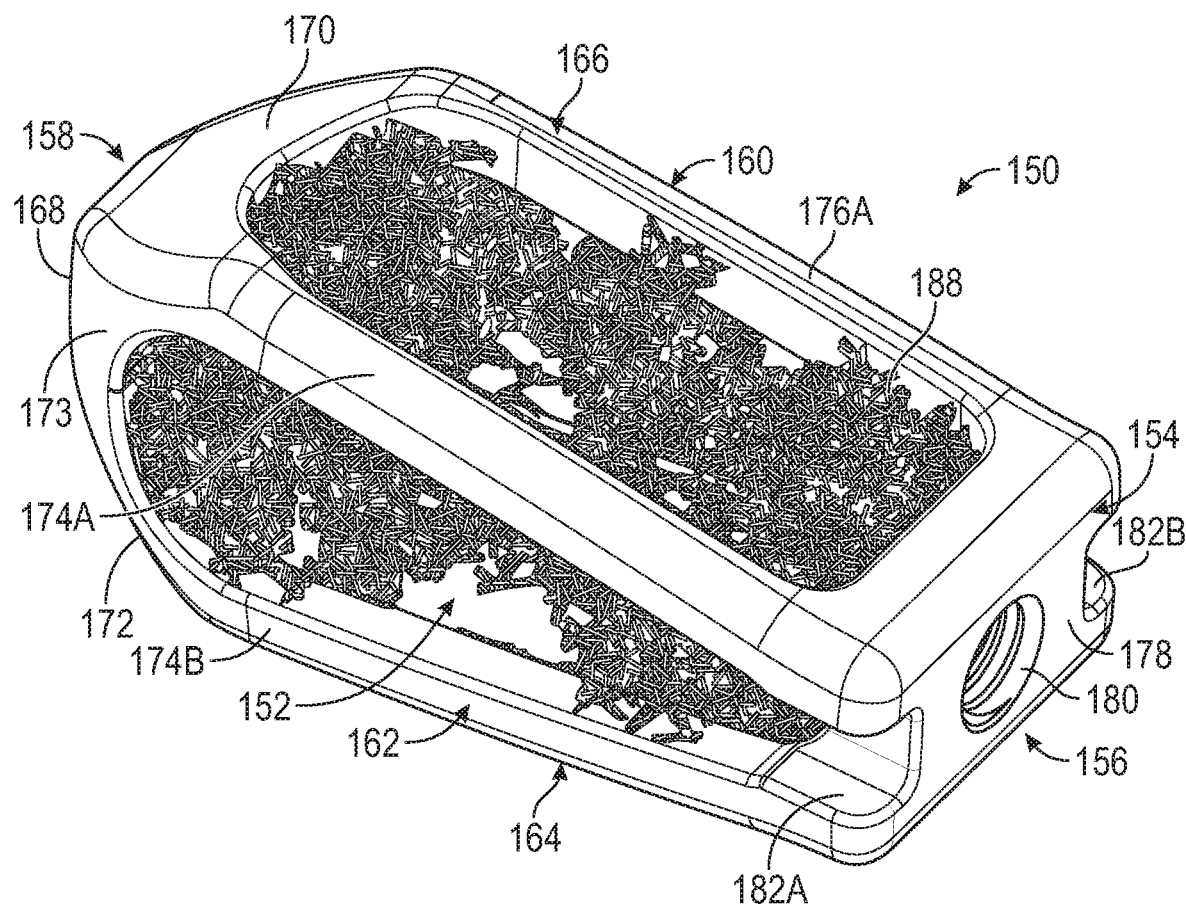
FIG. 22 is a perspective view of a Posterior Lumbar Interbody Fusion (PLIF) device.

FIG. 22 is a perspective view of Posterior Lumbar Interbody Fusion (PLIF) device 150 comprising porous structure 152 and cage 154. Cage 154 can comprise posterior handle-end 156, anterior insertion-end 158, medial-lateral side 160 and medial-lateral side 162. Bone-facing surfaces 164 and 166 can comprise superior or inferior surfaces. Cage 154 can comprise tip 168, first slide surface 170, second slide surface 171, third slide surface 172, fourth slide surface 173, medial-lateral rails 174A and 174B, medial-lateral rails 176A and 176B, and socket face 178. Socket face 178 can comprise bore 180 and notches 182A and 182B.

Figure 27:
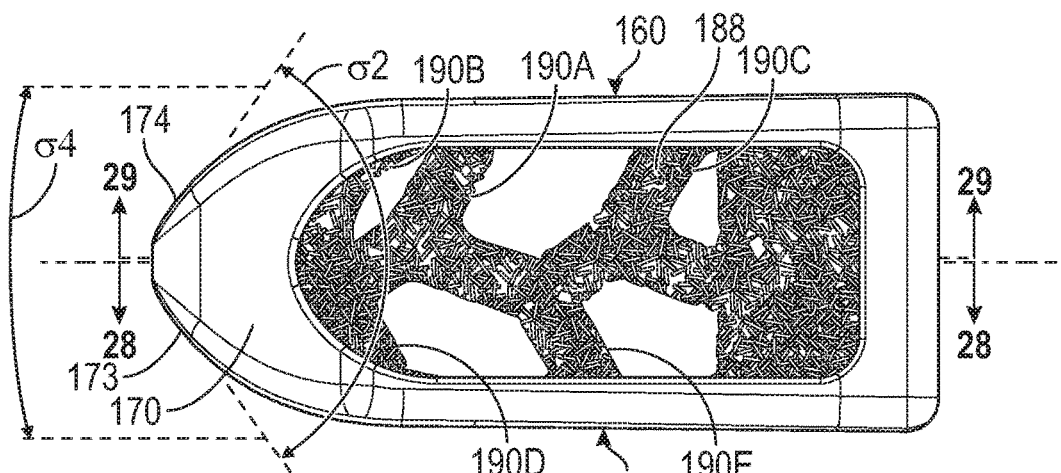
FIG. 27 is a superior view of the PLIF device of FIG. 22.

Slide surfaces 170-173, rails 174A-176B and socket face 178 can form a cage-like structure as described herein for supporting porous structure 152, as described herein. Porous structure 152 can comprise superior wall 188, which, as shown in FIG. 27, can include macro-pores 190A, 190B, 190C, 190D and 190E. Macro-pores 190A-190E can extend down through inferior wall 192. Pocket 194 can be located between superior wall 188 and inferior wall 192. Superior wall 188 and inferior wall 192 can be connected by sidewalls 195A and 195B anterior wall 196, which can include macro-pores 198A-198D. Additionally, pocket 194 can be provided with one or more support walls, such as support wall 30 of FIGS. 1 and 3.

Figure 23:
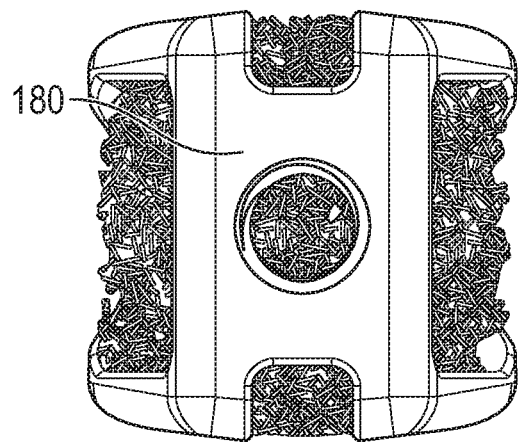
FIG. 23 is a handle-end view of the PLIF device of FIG. 22.
Figure 24:
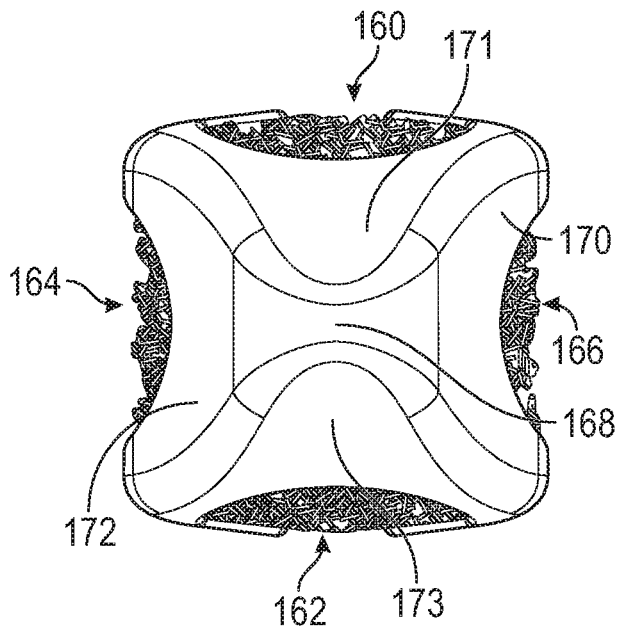
FIG. 24 is an insertion-end view of the PLIF device of FIG. 22.
Figure 25:
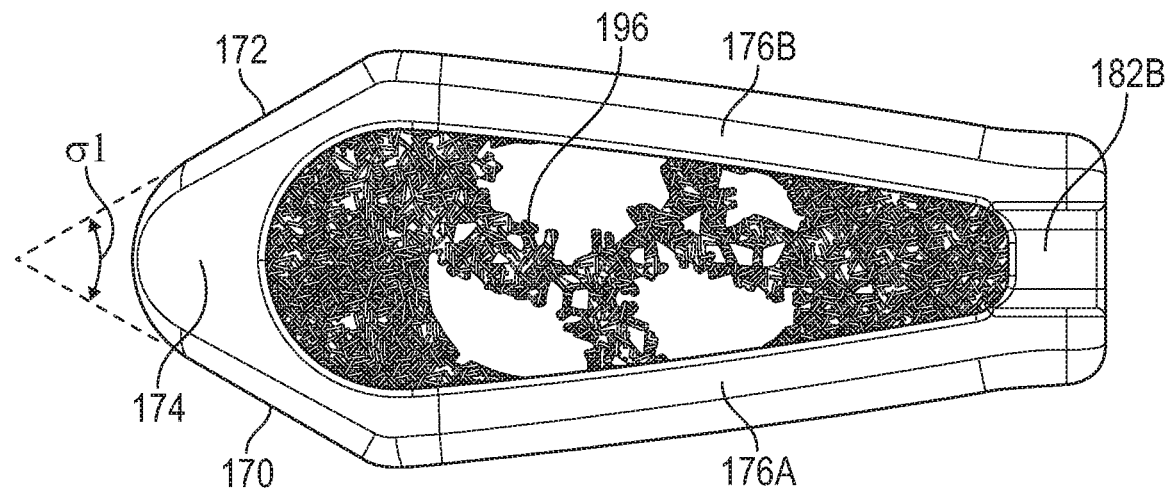
FIG. 25 is a medial-lateral view of the PLIF device of FIG. 22.
Figure 26:
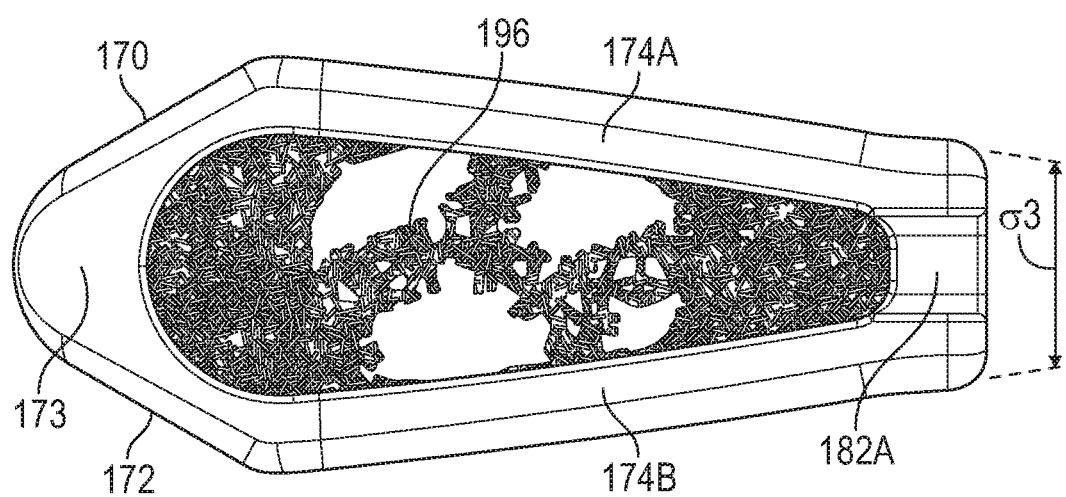
FIG. 26 is a medial-lateral view of the PLIF device of FIG. 22.
Figure 28:
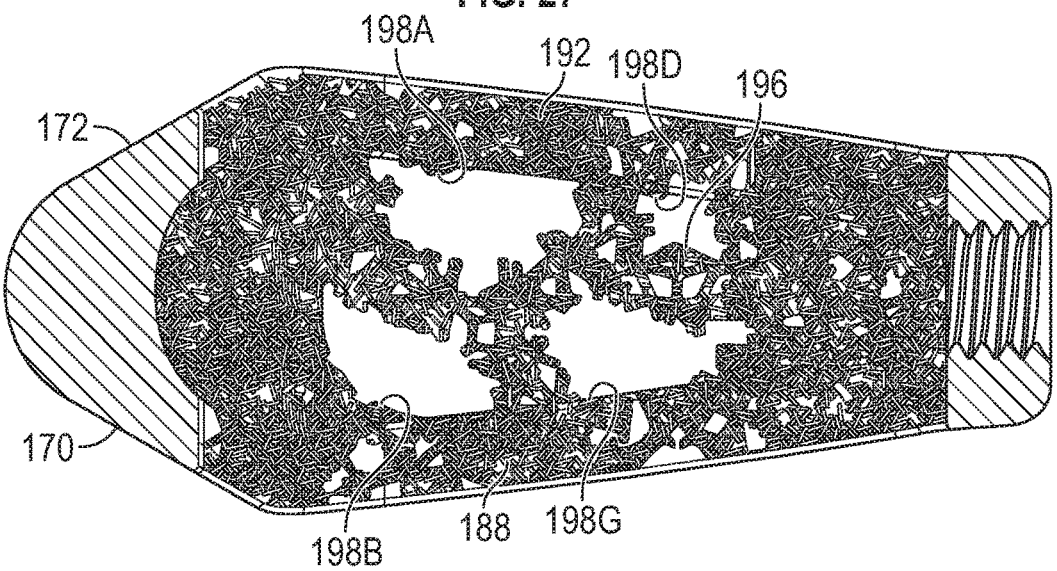
FIG. 28 is a cross-sectional view of the PLIF device of FIG. 27 taken at section 28-28 looking sideward.
Figure 29:
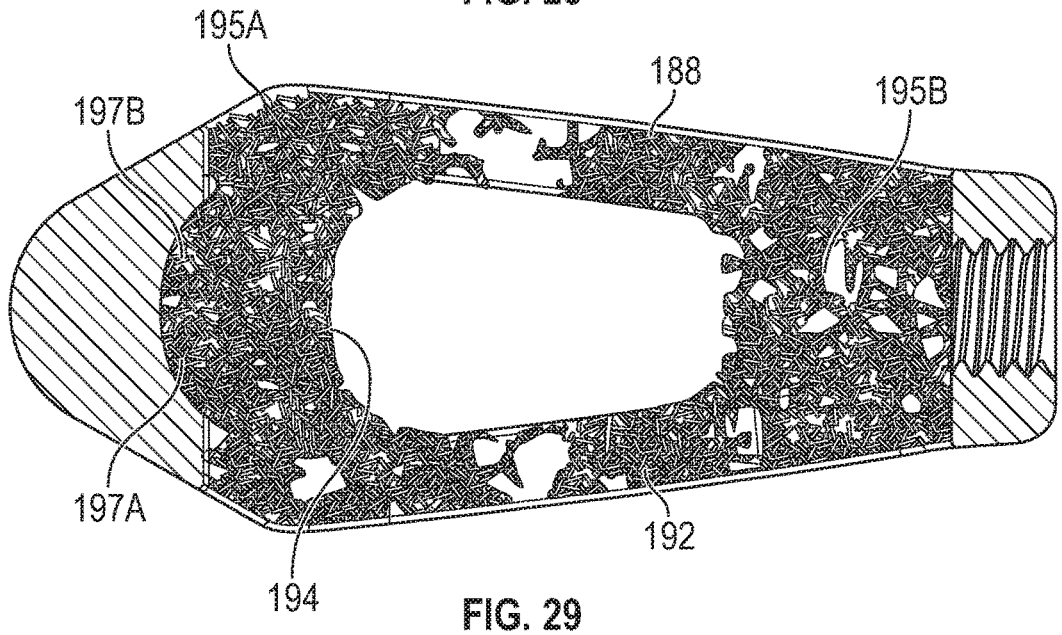
FIG. 29 is a cross-sectional view of the PLIF device of FIG. 27 taken at section 29-29 looking sideward.

FIG. 23 is a handle-end view of PLIF device 150 of FIG. 22 showing socket face 178. FIG. 24 is an insertion-end view of PLIF device 150 of FIG. 22 showing tip 168. FIG. 25 is a medial-lateral view of PLIF device of 150 FIG. 22 showing pocket 194 medial-lateral wall 196. FIG. 26 is a medial-lateral view of PLIF device 150 of FIG. 22 showing pocket 194 medial-lateral wall 196. FIG. 27 is a superior view of PLIF device 150 of FIG. 22 showing superior wall 188. FIG. 28 is a cross-sectional view of PLIF device 150 of FIG. 27 taken at section 28-28 looking sideward to show medial-lateral wall 196. FIG. 29 is a cross-sectional view of PLIF device 150 of FIG. 27 taken at section 29-29 looking sideward to show pocket 194. FIGS. 22-29 are discussed concurrently and mentioned specifically where applicable.

Porous structure 152 can be open on medial-lateral side 162 to allow placement of bone-growth material into porous structure 152 adjacent superior wall 188, inferior wall 192 and medial-lateral wall 196. Thus, inferior wall 192, sidewall 195A, superior wall 188 and sidewall 195B can encircle the bone-growth material with medial-lateral wall 196 inhibiting the bone-growth material from freely passing through porous structure 152. Furthermore, as shown in FIGS. 28 and 29, porous structure 152 can comprise bump 197A for residing in detent 197B in cage 104. Bump 197A and detent 197B can be configured to assist in retaining porous structure 152 within cage 154 such as when porous structure 152 is not monolithic with cage 154. Likewise, notches 182A and 182B can be used to support porous structure 152 and can permit growth of boney material into the interior of cage 154.

Second slide surface 171 and fourth slide surface 173 can be angled relative to medial-lateral sides 160 and 162 and can be angled toward each other near tip 168. Likewise, first slide surface 170 and third slide surface 172 can be angled relative to bone-facing surfaces 164 and 166 to come together at tip 168. Tip 168 can be rounded to join slide surfaces 170 and 172. Tip 168 can separate slide surfaces 171 and 173. As such, tip 168 can be pointed to provide an insertion tip for penetrating into and sliding past tissue, as described above. In an example, tip 168 has a pyramid shape and rails 174A-176B can have a right trapezoidal shape. Rails 174A-176B can be straight. In examples, medial-lateral rails 176A and 176B can be straight in the medial-lateral direction such that anterior side 160 is planer, and medial-lateral rails 174A and 174B can be straight in the medial-lateral direction such that posterior side 162 is planer.

As shown in FIGS. 25 and 26, slide surfaces 170 and 172 can be angled relative to each other at angle $\sigma1$. In examples, angle $\sigma1$ can be in the range of forty to ninety degrees. In the illustrated embodiment, angle $\sigma1$ is approximately forty degrees.

Similarly, as shown in FIG. 27 slide surfaces 171 and 173 can be angled to each other at angle $\sigma2$. In examples, angle $\sigma2$ can be in the range of forty-five to seventy-five degrees. In the illustrated embodiment, angle $\sigma2$ is approximately sixty degrees.

As shown in FIGS. 25 and 26, superior-inferior bone-facing surfaces 166 and 164 can be angled (e.g., lordosis) relative to each other at angle $\sigma3$. In examples, angle $\sigma3$ can be in the range of zero to thirty degrees. In the illustrated embodiment, angle $\sigma3$ is approximately twenty degrees.

As shown in FIG. 27, medial-lateral sides 160 and 162 can be angled relative to each other at angle $\sigma4$. In examples, angle $\sigma4$ can be in the range of zero to twenty degrees. In the illustrated embodiment, angle $\sigma4$ is approximately fifteen degrees.

Bore 180 of socket face 178 can form a port for receiving a tool that can be coupled to PLIF device 150 for insertion of PLIF device 150 between vertebrae. Bore 180 can permit the tool to be secured to cage 154 to facilitate insertion of PLIF device 150. Bore 180 can be located in socket face 178, which can be configured to couple rails 174A and 176A to rails 174B and 176B. In another configuration, socket face 178 can be made as part of porous structure 152 and tip 168 can include a slit or break so that rails 174A and 176A can be uncoupled from rails 174B and 176B.

PLIF device 150 is configured for insertion in between vertebrae from a posterior side of the spinal column. More specifically, PLIF device 150 is configured for insertion into a spinal column between a spinous process and an adjacent transverse process. PLIF device 150 can be configured, e.g., with different thicknesses, sized, widths, lengths to accommodate usage at different levels in the spinal column or in different sized patients. PLIF device 150 can inserted straight into the spinal column on one side of the spinal cord. In examples, a second PLIF device 150 can be inserted straight into the spinal column on the opposite side of the spinal column. An insertion device can be coupled to handle-end 156 and anterior end 158 can be pushed through tissue into the spinal column such that bone-facing surfaces 164 and 166 align with an inferior surface of a superior vertebra and a superior surface of an inferior vertebra.

Figure 30:
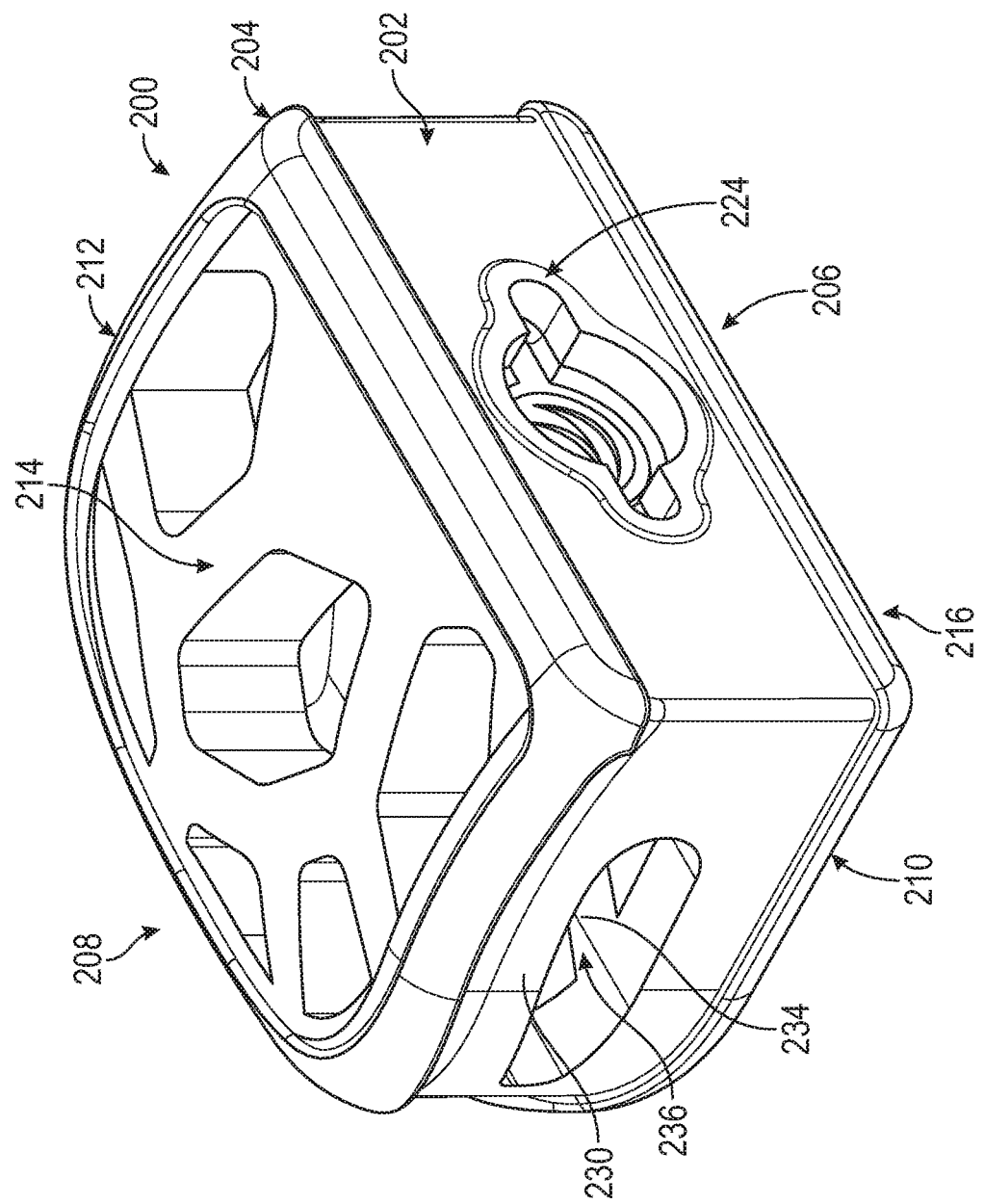
FIG. 30 is a perspective view of an anatomic Anterior Cervical Interbody Fusion (ACIF) device comprising a porous structure and a solid structure.

FIG. 30 is a perspective view of anatomic Anterior Cervical Interbody Fusion (ACIF) device 200 comprising porous structure 202 and solid structure 204. Solid structure 204 can comprise anterior handle-end 206, posterior insertion-end 208, medial-lateral side 210 and medial-lateral side 212. Bone-facing surfaces 214 and 216 can comprise superior or inferior surfaces. Solid structure 204 can comprise tip 218, superior rails 220A, 220B, 220C and 220D, inferior rails 222A, 222B, 222C and 222D and socket 224.

Figure 32:
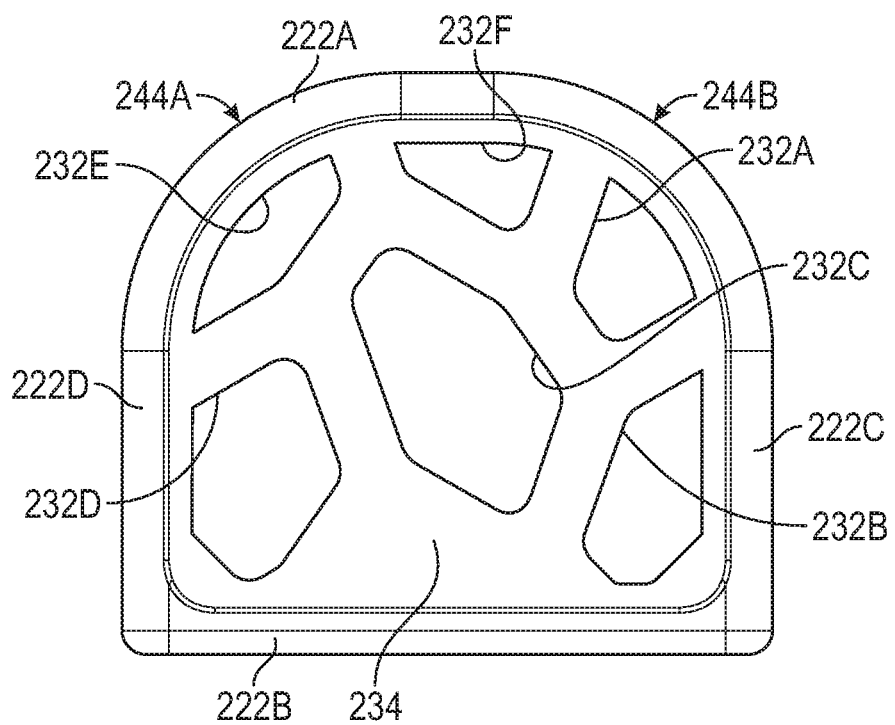
FIG. 32 is bottom view of the ACIF device of FIG. 30.

Rails 220A-220D, rails 222A-222D and socket 224 can form a cage-like structure as described herein for supporting porous structure 202, as described herein. Porous structure 202 can comprise superior wall 230, which, as shown in FIG. 32, can include macro-pores 232A, 232B, 232C, 232D, 232E and 232F. Macro-pores 232A-232F can extend down through inferior wall 234. Pocket 236 can be located between superior wall 230 and inferior wall 234 and can extend all the way across porous structure 202. However, only one medial-lateral side of porous structure 202 can have an opening for pocket 236. Superior wall 230 and inferior wall 234 can be connected by anterior wall 238A and posterior wall 238B. Additionally, pocket 236 can be provided with one or more support walls, such as support wall 30 of FIGS. 1 and 3.

Figure 31:
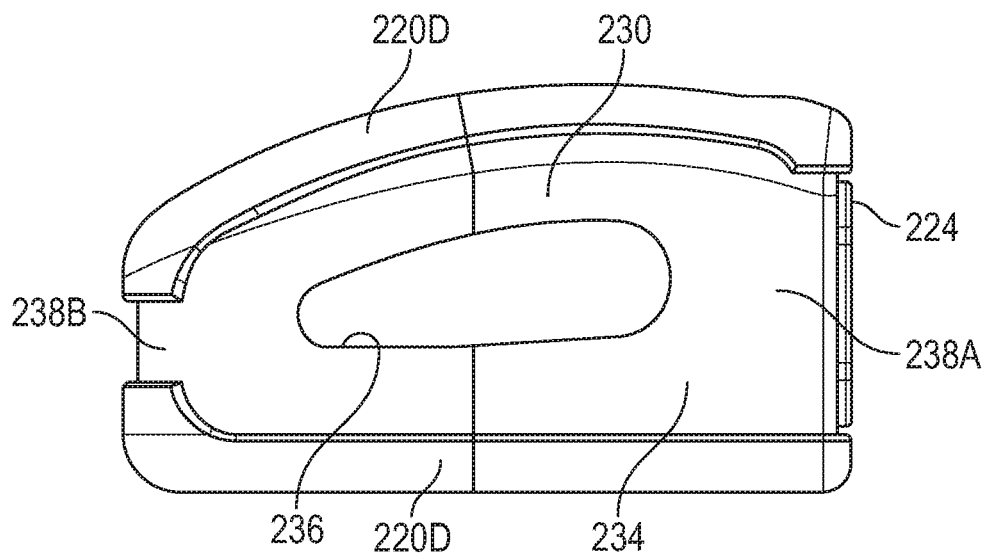
FIG. 31 is a side view of the ACIF device of FIG. 30.
Figure 33:
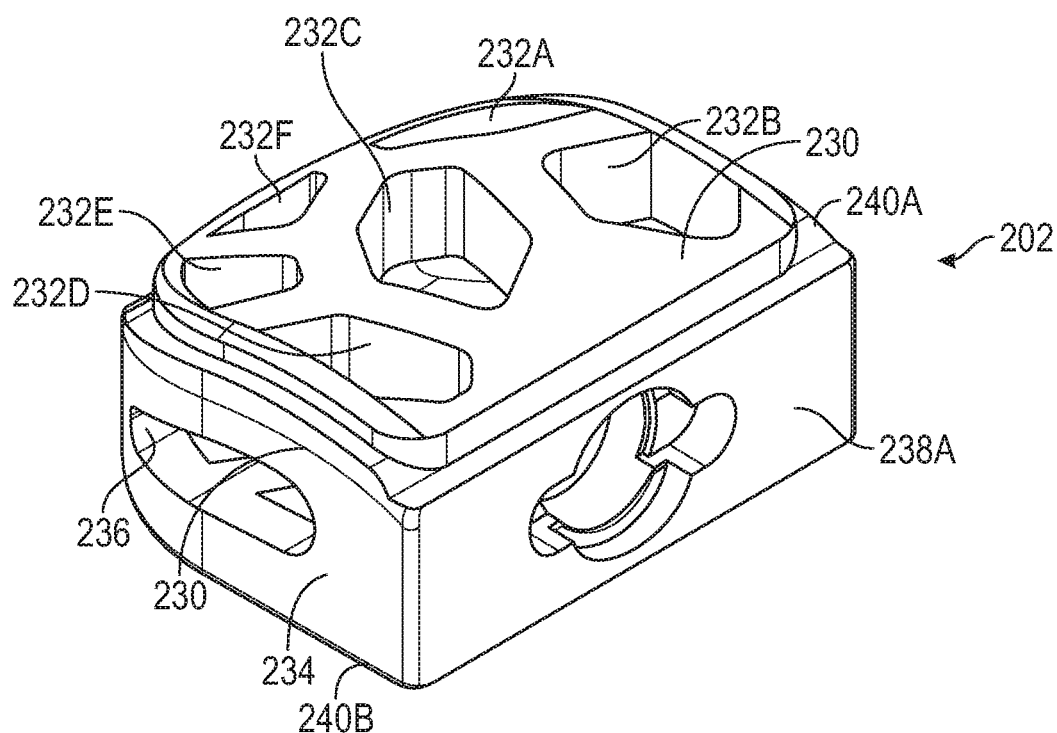
FIG. 33 is a perspective view of the porous structure of the ACIF device of FIG. 30.
Figure 34:
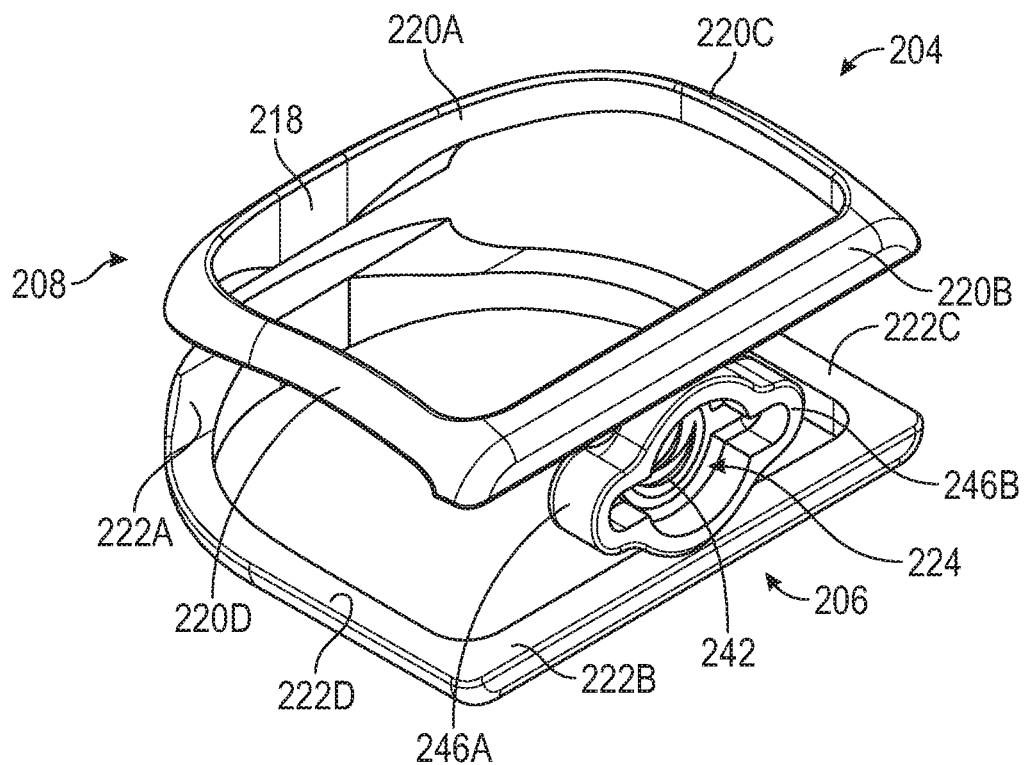
FIG. 34 is a perspective view of the solid structure of the ACIF device of FIG. 30.

FIG. 31 is a side view of ACIF device 200 of FIG. 30 showing pocket 236. FIG. 32 is bottom view of ACIF device 200 of FIG. 30 showing macro-pores 232A-232F. FIG. 33 is a perspective view of porous structure 202 of ACIF device 200 of FIG. 30 showing superior wall 230 and inferior wall 234 bounding pocket 236. FIG. 34 is a perspective view of solid structure 204 of ACIF device 200 of FIG. 30 showing rails 220A-222D. FIGS. 30-34 are discussed concurrently and mentioned specifically where applicable.

Porous structure 202 can be open on medial-lateral sides 210 and 212 to allow placement of bone-growth material into porous structure 202 adjacent superior wall 230 and inferior wall 234. Thus, inferior wall 234, anterior wall 238A, superior wall 230 and posterior wall 238B can encircle the bone-growth material within pocket 236. Furthermore, as shown in FIG. 33, porous structure 202 can comprise superior shoulder 240A and inferior shoulder 240B, which can be configured to assist in retaining porous structure 202 within solid structure 204, such as by producing a snap-fit interface or surfaces for forming a weld or for providing increased surface area for porous structure 202 to join to solid structure 204 such as when porous structure 202 is not monolithic with solid structure 204.

ACIF device 200 can be shaped for use in the anatomic or non-lordotic regions of the spinal column. However, ACIF device 200 can be configured to provide a lordosis correction of 6 degrees. ACIF device 200 can comprise a generally rectilinear body with medial-lateral side 210, medial-lateral side 212, bone-facing surface 216 including inferior wall 234, anterior wall 238A and posterior wall 238B being generally flat. Anterior wall 238A can be disposed at right angles to bone-facing surfaces 214 and 216 and medial-lateral sides 210 and 212. Posterior wall 238B can be disposed at right angles to bone-facing surfaces 214 and 216 and medial-lateral sides 210 and 212. However, medial-lateral sides 210 and 212 can be curved to blend into posterior wall 238B. In an example, surfaces 244A and 244B can comprise circular arc segments. In examples, surfaces 294A and 294B can be circular quadrants. Bone-facing surface 214 including superior wall 230 can be curved or hump-shaped, such as to fit against the natural curvature of the inferior side of a vertebra thereby increasing surface area contact to promote bone in-growth. Anterior wall 238A can be shorter than posterior wall 238B. As such, ACIF device 200 can be shaped to be pushed through tissue.

Socket 224 can form a port for receiving a tool that can be coupled to ACIF device 200 for insertion of ACIF device 200 between vertebrae. Socket 224 can include bore 242 that can permit the tool to be secured to solid structure 204 to facilitate insertion of ACIF device 200. Bore 242 can comprise a threaded port. Socket 224 can additionally include features to prevent movement of socket 224 relative to porous structure 202. For example, socket 224 can include lobes 246A and 246B. In examples, socket 224 can be attached to rails 220B and 222B. In other examples, socket 224 can be spaced from rails 220B and 222B.

ACIF device 200 is configured for insertion in between vertebrae from an anterior side of the spinal column. More specifically, ACIF device 200 is configured for insertion into a spinal column, from an anterior or front approach, straight between the main bodies of adjacent vertebrae in the lower cervical spine region. ACIF device 200 can be configured, e.g., with different thicknesses, sized, widths, lengths to accommodate usage at different levels in the spinal column or in different sized patients. An insertion device can be coupled to handle-end 206 and posterior end 208 can be pushed through tissue into the spinal column such that bone-facing surfaces 214 and 216 align with an inferior surface of a superior vertebra and a superior surface of an inferior vertebra, such that ACIF device 200 can align with the posterior wall of the adjacent vertebrae. ACIF device 200 can be produced in different sizes, e.g., thicknesses of porous structure 202, for use in different levels of the spine.

Figure 35:
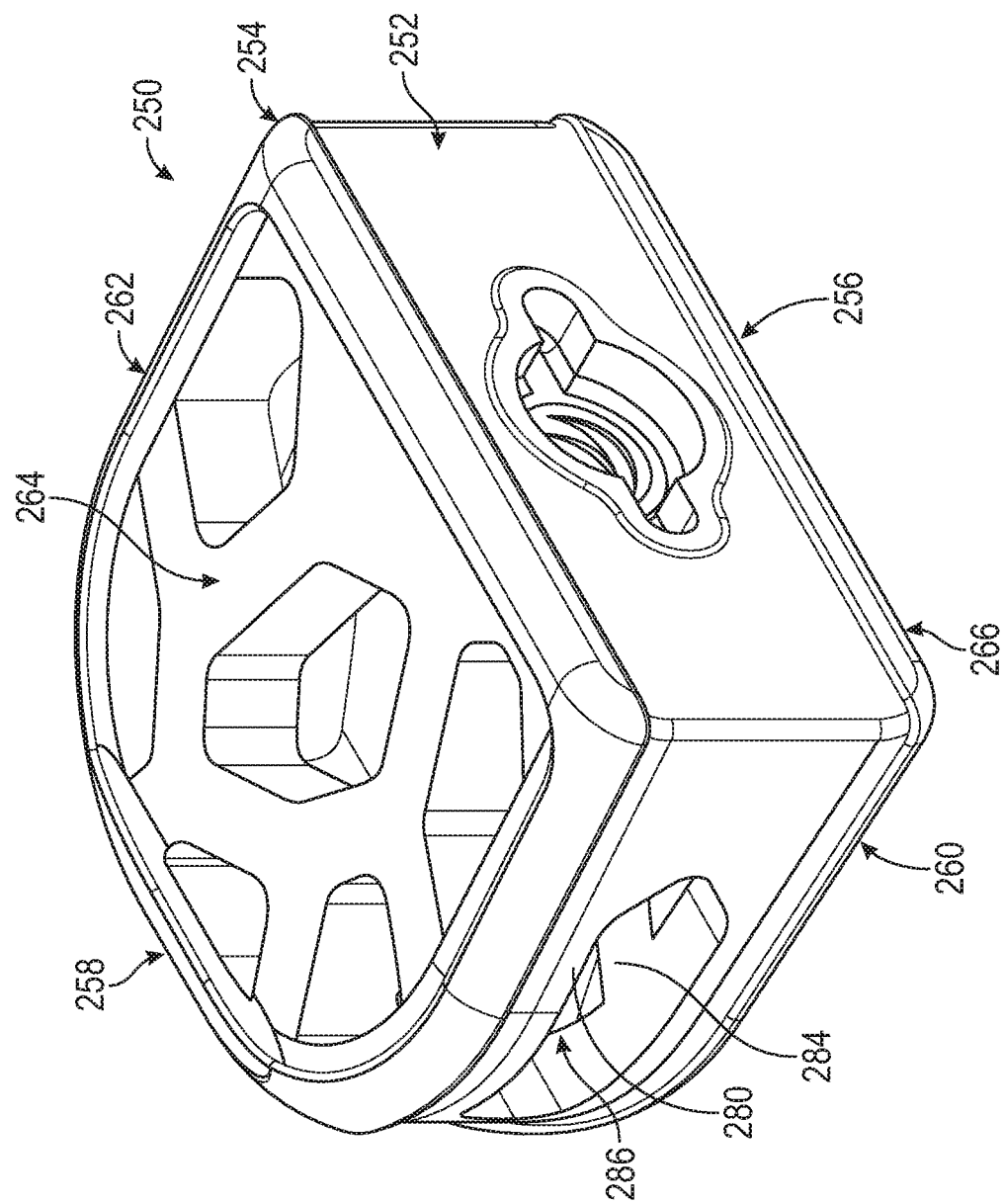
FIG. 35 is a perspective view of a lordotic Anterior Cervical Interbody Fusion (ACIF) device comprising a porous structure and a solid structure.

FIG. 35 is a perspective view of lordotic Anterior Cervical Interbody Fusion (ACIF) device 250 comprising porous structure 252 and solid structure 254. Solid structure 254 can comprise anterior handle-end 256, posterior insertion-end 258, medial-lateral side 260 and medial-lateral side 262. Bone-facing surfaces 264 and 266 can comprise superior or inferior surfaces. Solid Structure 254 can comprise tip 268, superior rails 270A, 270B, 270C and 270D, inferior rails 272A, 272B, 272C and 272D and socket 274.

Figure 37:
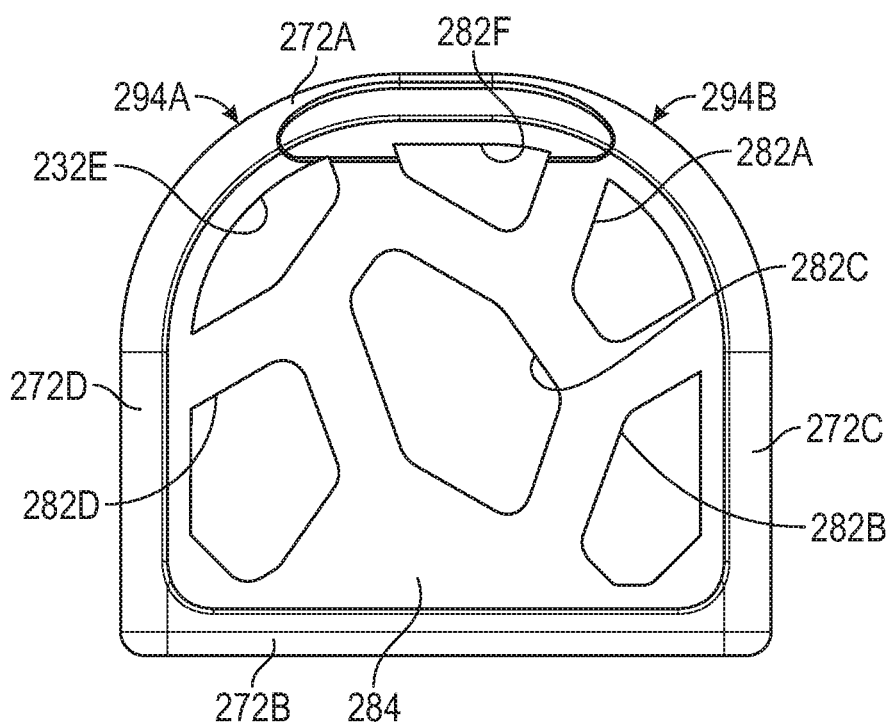
FIG. 37 is bottom view of the ACIF device of FIG. 35.

Rails 270A-270D, rails 272A-272D and socket 274 can form a cage-like structure as described herein for supporting porous structure 252, as described herein. Porous structure 252 can comprise superior wall 280, which, as shown in FIG. 37, can include macro-pores 282A, 282B, 282C, 282D, 282E and 282F. Macro-pores 282A-282F can extend down through inferior wall 284. Pocket 286 can be located between superior wall 280 and inferior wall 284 and can extend all the way across porous structure 252. As described above, the scale of macro-pores 282A-282F and the size of pocket 286 can be scaled to the size of porous structure 252, such that the larger porous structure is, the greater macro-pores 282A-282F and pocket 286 can be. However, only one medial-lateral side of porous structure 252 can have an opening for pocket 286. Superior wall 280 and inferior wall 284 can be connected by anterior wall 288A and posterior wall 288B. Additionally, pocket 286 can be provided with one or more support walls, such as support wall 30 of FIGS. 1 and 3.

Figure 36:
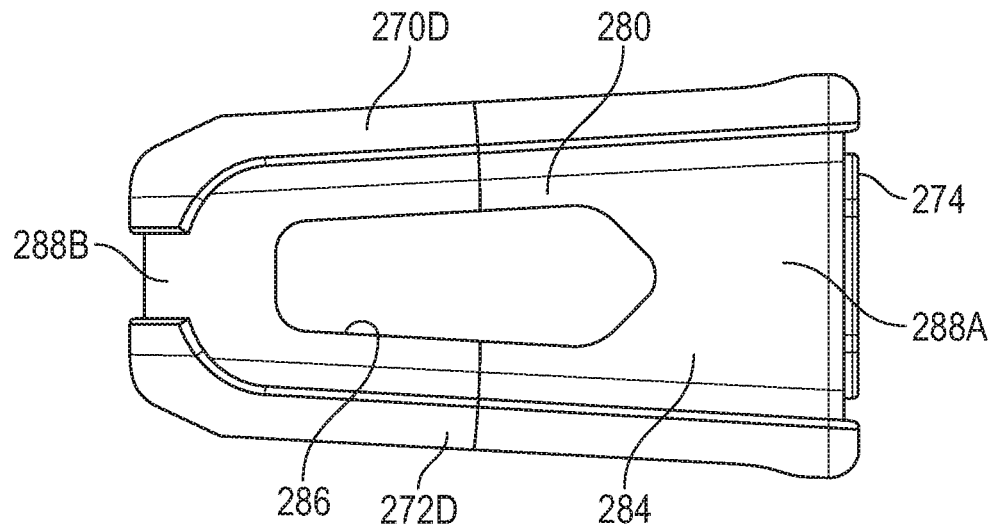
FIG. 36 is a side view of the ACIF device of FIG. 35.
Figure 38:
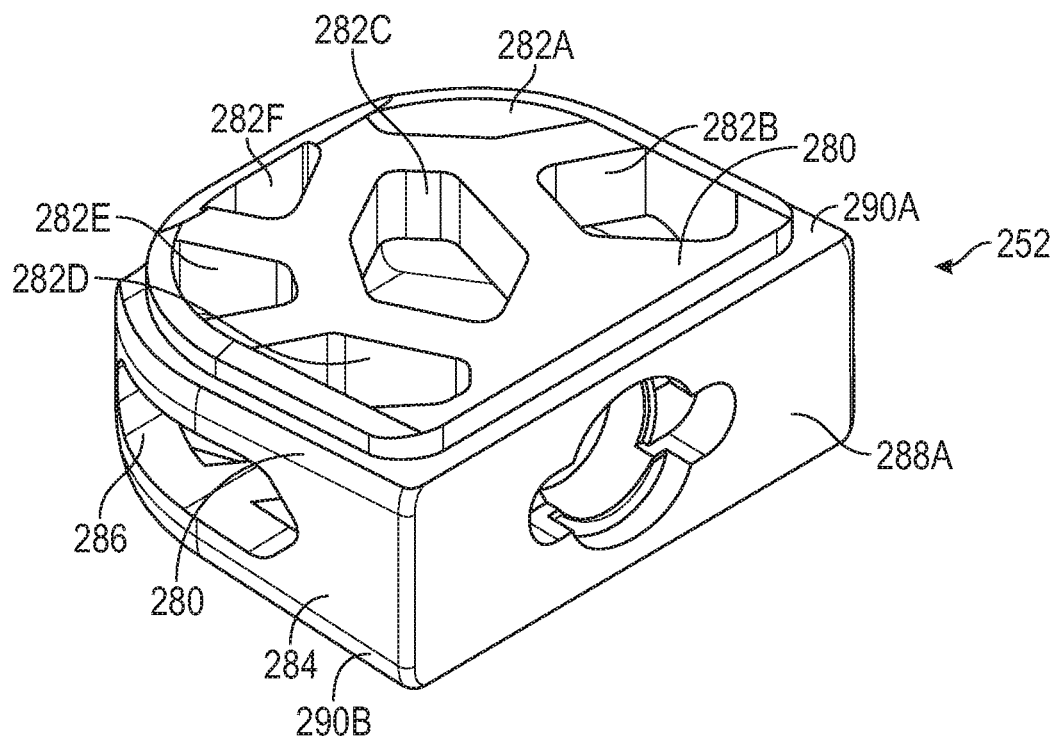
FIG. 38 is a perspective view of the porous structure of the ACIF device of FIG. 35.
Figure 39:
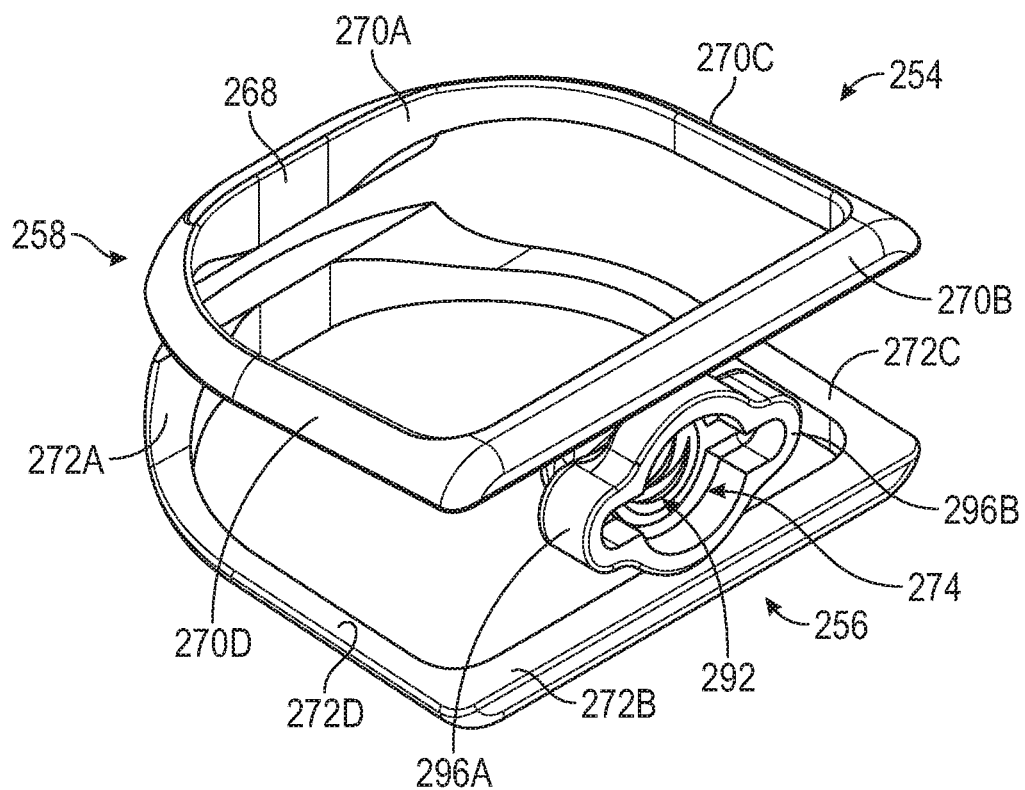
FIG. 39 is a perspective view of the solid structure of the ACIF device of FIG. 35.

FIG. 36 is a side view of ACIF device 250 of FIG. 35 showing pocket 286. FIG. 37 is bottom view of ACIF device 250 of FIG. 35 showing macro-pores 282A-282F. FIG. 38 is a perspective view of porous structure 252 of ACIF device 250 of FIG. 35 showing superior wall 280 and inferior wall 234 bounding pocket 286. FIG. 39 is a perspective view of solid structure 254 of ACIF device 250 of FIG. 35 showing rails 270A-272D. FIGS. 35-39 are discussed concurrently and mentioned specifically where applicable.

Porous structure 252 can be open on medial-lateral sides 260 and 262 to allow placement of bone-growth material into porous structure 252 adjacent superior wall 280 and inferior wall 284. Thus, inferior wall 284, anterior wall 288A, superior wall 280 and posterior wall 288B can encircle the bone-growth material within pocket 286. Furthermore, as shown in FIG. 38, porous structure 252 can comprise superior shoulder 290A and inferior shoulder 290B, which can be configured to assist in retaining porous structure 252 within solid structure 254, such as by producing a snap-fit interface or surfaces for forming a weld or for providing increased surface area for porous structure 252 to join to solid structure 254 such as when porous structure 252 is not monolithic with solid structure 254.

ACIF device 250 can be shaped for use in the lordotic regions of the spinal column. ACIF device 250 can be configured to provide a lordosis correction of 6 degrees. ACIF device 250 can comprise a generally rectilinear body with medial-lateral side 260, medial-lateral side 262, bone-facing surface 264 including superior wall 286, bone-facing surface 266 including inferior wall 284, anterior wall 288A and posterior wall 288B being generally flat. Anterior wall 288A can be disposed at right angles to bone-facing surfaces 264 and 266 and medial-lateral sides 260 and 262. Posterior wall 288B can be disposed at right angles to bone-facing surfaces 264 and 266 and medial-lateral sides 260 and 262. However, medial-lateral sides 260 and 262 can be curved to blend into posterior wall 288B. In an example, surfaces 294A and 294B can comprise circular arc segments. In examples, surfaces 294A and 294B can be circular quadrants. Bone-facing surface 264 including superior wall 280 and bone-facing surface 266 including inferior wall 284 can be flat, such as to fit against the natural curvature of the inferior and superior sides of adjacent vertebrae in the lordotic region of the spine thereby increasing surface area contact to promote bone in-growth. Anterior wall 288A can be shorter than posterior wall 288B. As such, ACIF device 250 can be shaped to be pushed through tissue.

Socket 274 can form a port for receiving a tool that can be coupled to ACIF device 250 for insertion of ACIF device 250 between vertebrae. Socket 274 can include bore 292 that can permit the tool to be secured to solid structure 254 to facilitate insertion of ACIF device 250. Bore 292 can comprise a threaded port. Socket 274 can additionally include features to prevent movement of socket 274 relative to porous structure 252. For example, socket 274 can include lobes 296A and 296B. In examples, socket 274 can be attached to rails 270B and 272B. In other examples, socket 274 can be spaced from rails 270B and 272B.

ACIF device 250 is configured for insertion in between vertebrae from an anterior side of the spinal column. More specifically, ACIF device 250 is configured for insertion into a spinal column, from an anterior or front approach, straight between the main bodies of adjacent vertebrae in the lower cervical spine region. ACIF device 250 can be configured, e.g., with different thicknesses, sized, widths, lengths to accommodate usage at different levels in the spinal column or in different sized patients. ACIF device 250 can inserted straight into the spinal column directly in front of the spinal column. An insertion device can be coupled to handle-end 256 and posterior end 258 can be pushed through tissue into the spinal column such that bone-facing surfaces 264 and 266 align with an inferior surface of a superior vertebra and a superior surface of an inferior vertebra, such that ACIF device 200 can align with the posterior wall of the adjacent vertebrae. ACIF device 250 can be produced in different sizes, e.g., thicknesses of porous structure 252, for use in different levels of the spine.

Various Notes & Examples

Example 1 can include or use subject matter such as an interbody implant comprising a first cage comprising an anterior segment, a medial segment, a posterior segment and a lateral segment contiguously connected to each other to define an interior space; and a porous structure located in the interior space and bounded by the cage, the porous structure comprising opposed superior and inferior surfaces exposed through the first cage; an internal cavity located in an interior of the porous structure; and a plurality of ports connecting the internal cavity to the superior and inferior surfaces.

Example 2 can include, or can optionally be combined with the subject matter of Example 1, to optionally include a porous structure that can further comprise an anterior-posterior opening into the internal cavity.

Example 3 can include, or can optionally be combined with the subject matter of one or any combination of Examples 1 or 2 to optionally include an anterior-posterior opening that can be located on an anterior surface of the porous structure.

Example 4 can include, or can optionally be combined with the subject matter of one or any combination of Examples 1 through 3 to optionally include a porous structure that can further comprise a posterior surface including a plurality of ports.

Example 5 can include, or can optionally be combined with the subject matter of one or any combination of Examples 1 through 4 to optionally include a porous support wall extending across the internal cavity in a superior-inferior direction.

Example 6 can include, or can optionally be combined with the subject matter of one or any combination of Examples 1 through 5 to optionally include a support wall that can be located at a medial-lateral center of the interbody implant.

Example 7 can include, or can optionally be combined with the subject matter of one or any combination of Examples 1 through 6 to optionally include a plurality of ports that can comprise a plurality of hexa-lobular openings extending from an exterior of the porous structure to the internal cavity.

Example 8 can include, or can optionally be combined with the subject matter of one or any combination of Examples 1 through 7 to optionally include each of the plurality of ports comprising a cross-sectional area larger than a pore size of the porous structure.

Example 9 can include, or can optionally be combined with the subject matter of one or any combination of Examples 1 through 8 to optionally include a porous structure that can comprise a plurality of ligaments defining open spaces therebetween, the ligaments forming a matrix of continuous channels having no dead ends.

Example 10 can include, or can optionally be combined with the subject matter of one or any combination of Examples 1 through 9 to optionally include a second cage having anterior, medial, posterior and lateral segments contiguously connected to each other to define an additional interior space, wherein the porous structure can be located within the additional interior space.

Example 11 can include, or can optionally be combined with the subject matter of one or any combination of Examples 1 through 10 to optionally include a first cage and a second cage that can be uncoupled in a superior-inferior direction.

Example 12 can include, or can optionally be combined with the subject matter of one or any combination of Examples 1 through 11 to optionally include a threaded socket located on a medial or lateral side of the interbody implant, the threaded socket having a superior portion located on the first cage and an inferior portion located on the second cage.

Example 13 can include, or can optionally be combined with the subject matter of one or any combination of Examples 1 through 12 to optionally include a wedge structure located on an end of the interbody implant.

Example 14 can include, or can optionally be combined with the subject matter of one or any combination of Examples 1 through 13 to optionally include a wedge structure that can comprise opposing tapered surfaces that form a thinnest portion of the interbody implant in a superior-inferior direction.

Example 15 can include, or can optionally be combined with the subject matter of one or any combination of Examples 1 through 14 to optionally include a first cage that can define a superior-most surface of the interbody implant flush with a superior-most portion of the porous structure, and a second cage that can define an inferior-most surface of the interbody implant flush with an inferior-most portion of the porous structure.

Example 16 can include, or can optionally be combined with the subject matter of one or any combination of Examples 1 through 15 to optionally include an interbody implant that can define an angle between the superior-most surface and the inferior-most surface.

Example 17 can include, or can optionally be combined with the subject matter of one or any combination of Examples 1 through 16 to optionally include an angle that can be in the range of approximately six degrees to approximately thirty degrees.

Example 18 can include, or can optionally be combined with the subject matter of one or any combination of Examples 1 through 17 to optionally include anterior segments of first and second cages that can be curved so that an anterior side of the interbody implant is convex, and posterior segments of the first and second cages can be curved so that a posterior side of the interbody implant is concave.

Example 19 can include, or can optionally be combined with the subject matter of one or any combination of Examples 1 through 18 to optionally include a first cage and a second cage that can be connected by a socket.

Example 20 can include, or can optionally be combined with the subject matter of one or any combination of Examples 1 through 19 to optionally include a superior wall that can have a bore, an inferior wall that can have a bore, a first longitudinal surface connecting the superior and inferior walls, and a second longitudinal surface connecting the superior and inferior walls, wherein the first and second longitudinal surfaces can be disposed at an angle to each other.

Example 21 can include, or can optionally be combined with the subject matter of one or any combination of Examples 1 through 20 to optionally include a first cage and a second cage that can be angled toward each other at an insertion end of the interbody implant and the first cage and the second cage can come together at a rounded tip at the insertion end.

Example 22 can include, or can optionally be combined with the subject matter of one or any combination of Examples 1 through 21 to optionally include an insertion end and a coupling end, and a first cage and a second cage that can be joined at the insertion end and the coupling end.

Example 23 can include, or can optionally be combined with the subject matter of one or any combination of Examples 1 through 22 to optionally include an insertion end that can comprise a pyramid and a coupling end that can include a socket.

Example 24 can include, or can optionally be combined with the subject matter of one or any combination of Examples 1 through 23 to optionally include an insertion end that can be thicker than a coupling end.

Example 25 can include, or can optionally be combined with the subject matter of one or any combination of Examples 1 through 24 to optionally include a socket piece embedded into the porous structure.

Example 26 can include, or can optionally be combined with the subject matter of one or any combination of Examples 1 through 25 to optionally include a socket piece that can be connected to a first cage and a second cage.

Example 27 can include, or can optionally be combined with the subject matter of one or any combination of Examples 1 through 26 to optionally include a superior surface of the porous structure that can be curved.

Example 28 can include, or can optionally be combined with the subject matter of one or any combination of Examples 1 through 27 to optionally include a superior-inferior stiffness of the interbody implant is defined by the porous structure.

Example 29 can include, or can optionally be combined with the subject matter of one or any combination of Examples 1 through 28 to optionally include a first cage that can be fabricated from a solid metal material and a porous structure that can be fabricated from a porous metal material having a porosity mimicking that of natural bone.

Example 30 can include, or can optionally be combined with the subject matter of one or any combination of Examples 1 through 29 to optionally include a first cage that can comprise about 15% by volume of the interbody implant.

Example 31 can include or use subject matter such as a method of implanting an interbody implant between adjacent bones to promote bone in-growth and the method can comprise inserting the interbody implant between adjacent bones, the interbody implant comprising a porous structure comprising a monolithic body formed of a porous material replicating porosity of human bone; an interior cavity; and a plurality of openings in the monolithic body extending from the interior cavity to an exterior of the monolithic body; and a cage structure circumscribing a portion of the monolithic body in a transverse plane; positioning the plurality of openings against surfaces of the bones to allow for in-growth; and permitting the porous structure to compress in a superior-inferior direction between the bones and within the cage structure to stimulate biological bone growth within the bones.

Example 32 can include, or can optionally be combined with the subject matter of Example 31, to optionally include inserting the interbody implant between adjacent bones by sliding a wedge-shaped medial-lateral end of the interbody implant along tissue surrounding the bones.

Example 33 can include, or can optionally be combined with the subject matter of one or any combination of Examples 31 or 32 to optionally include disposing bone cement or bone graft material within the interior cavity before inserting the interbody implant between adjacent bones.

Example 34 can include, or can optionally be combined with the subject matter of one or any combination of Examples 31 through 33 to optionally include inserting the interbody implant between adjacent bones by attaching a tool to a socket located on a medial-lateral end of the interbody implant, the socket formed entirely in the cage structure.

Example 35 can include, or can optionally be combined with the subject matter of one or any combination of Examples 31 through 34 to optionally include a cage structure that can comprise: a first cage defining a superior-most surface of the interbody implant flush with a superior-most portion of the porous structure; and a second cage defining an inferior-most surface of the interbody implant flush with an inferior-most portion of the porous structure; wherein the first cage and the second cage are separated in a superior-inferior direction and do not contact each other.

Example 36 can include, or can optionally be combined with the subject matter of one or any combination of Examples 31 through 35 to optionally include permitting the porous structure to compress in a superior-inferior direction between the bones and within the cage structure by compressing the porous structure via movement of the bones.

Example 37 can include, or can optionally be combined with the subject matter of one or any combination of Examples 31 through 36 to optionally include inserting the interbody implant between adjacent bones by inserting the interbody implant such that a support wall within the interior cavity is medially-laterally centered between the adjacent bones.

Example 38 can include or use subject matter such as an intervertebral implant for lateral insertion and the intervertebral implant can comprise a porous structure formed of a porous material, the porous structure shaped to define an interior cavity; and a plurality of longitudinal passages extending through the porous structure to intersect the internal cavity; a first cerclage cage horizontally surrounding the porous structure; and a second cerclage cage horizontally surrounding the porous structure uncoupled from the first cerclage cage such that a longitudinal stiffness of the intervertebral implant is defined by the porous structure.

Example 39 can include, or can optionally be combined with the subject matter of Example 38, to optionally include a porous structure that can comprise a superior panel including a plurality of openings extending through the superior panel to partially define the plurality of longitudinal passages; an inferior panel including a plurality of openings extending through the inferior panel to partially define the plurality of longitudinal passages; and a middle panel separating the superior panel and the inferior panel to define the interior cavity.

Example 40 can include, or can optionally be combined with the subject matter of one or any combination of Examples 38 or 39 to optionally include a first cerclage cage and a second cerclage cage that can include ramped end portions to provide the intervertebral implant with a wedge-shaped insertion end.

Example 41 can include, or can optionally be combined with the subject matter of one or any combination of Examples 38 through 40 to optionally include a first cerclage cage and a second cerclage cage that can each include a partial coupling socket that together form a socket configured to receive an insertion tool.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An interbody implant comprising:
a first cage comprising an anterior segment, a medial segment, a posterior segment and a lateral segment contiguously connected to each other to define an interior space; and
a porous structure located in the interior space and bounded by the cage, the porous structure comprising:
opposed superior and inferior surfaces exposed through the first cage;
an internal cavity located in an interior of the porous structure; and
a plurality of ports connecting the internal cavity to the superior and inferior surfaces.

2. The interbody implant of claim 1, wherein the porous structure further comprises an anterior-posterior opening into the internal cavity.

3. The interbody implant of claim 2, wherein:
the anterior-posterior opening is located on an anterior surface of the porous structure; and
the porous structure further comprises a posterior surface including a plurality of ports.

4. The interbody implant of claim 1, further comprising a porous support wall extending across the internal cavity in a superior-inferior direction.

5. The interbody implant of claim 4, wherein the support wall is located at a medial-lateral center of the interbody implant.

6. The interbody implant of claim 1, wherein:
the plurality of ports comprise a plurality of hexa-lobular openings extending from an exterior of the porous structure to the internal cavity; and
each of the plurality of ports comprises a cross-sectional area larger than a pore size of the porous structure.

7. The interbody implant of claim 1, wherein the porous structure comprises a plurality of ligaments defining open spaces therebetween, the ligaments forming a matrix of continuous channels having no dead ends, wherein the first cage is fabricated from a solid metal material and the porous structure is fabricated from a porous metal material and has a porosity mimicking that of natural bone.

8. The interbody implant of claim 1, further comprising a second cage having anterior, medial, posterior and lateral segments contiguously connected to each other to define an additional interior space, wherein the porous structure is located within the additional interior space.

9. The interbody implant of claim 8, wherein the first cage and the second cage are uncoupled in a superior-inferior direction.

10. The interbody implant of claim 9, further comprising a threaded socket located on a medial or lateral side of the interbody implant, the threaded socket having a superior portion located on the first cage and an inferior portion located on the second cage.

11. The interbody implant of claim 8, further comprising a wedge structure located on an end of the interbody implant, wherein the wedge structure comprises opposing tapered surfaces that form a thinnest portion of the interbody implant in a superior-inferior direction.

12. The interbody implant of claim 8, wherein:
the first cage defines a superior-most surface of the interbody implant flush with a superior-most portion of the porous structure; and
the second cage defines an inferior-most surface of the interbody implant flush with an inferior-most portion of the porous structure.

13. The interbody implant of claim 12, wherein the interbody implant defines an angle between the superior-most surface and the inferior-most surface, wherein the angle is in the range of approximately six degrees to approximately thirty degrees.

14. The interbody implant of claim 8, wherein:
the anterior segments of the first and second cages are curved so that an anterior side of the interbody implant is convex;
the posterior segments of the first and second cages are curved so that a posterior side of the interbody implant is concave; and
a superior surface of the porous structure is curved.

15. The interbody implant of claim 14, wherein the first cage and the second cage are connected by a socket, wherein the socket comprises a swivel coupling comprising:
a superior wall having a bore;
an inferior wall having a bore;
a first longitudinal surface connecting the superior and inferior walls; and
a second longitudinal surface connecting the superior and inferior walls;
wherein the first and second longitudinal surfaces are disposed at an angle to each other.

16. The interbody implant of claim 14, wherein the interbody implant defines an insertion end and a coupling end and the first cage and the second cage are joined at the insertion end and the coupling end, wherein the first cage and the second cage are angled toward each other at the insertion end of the interbody implant and the first cage and the second cage come together at a rounded tip at the insertion end.

17. The interbody implant of claim 16, wherein the insertion end comprises a pyramid and the coupling end includes a socket, wherein the insertion end is thicker than the coupling end.

18. The interbody implant of claim 14, further comprising a socket piece embedded into the porous structure, wherein the socket piece is connected to the first cage and the second cage.

19. The interbody implant of claim 1, wherein a superior-inferior stiffness of the interbody implant is defined by the porous structure.

20. The interbody implant of claim 1, wherein the first cage comprises 15% by volume of the interbody implant.

21. An intervertebral implant for lateral insertion, the intervertebral implant comprising:
a porous structure formed of a porous material, the porous structure shaped to define:
an interior cavity; and
a plurality of longitudinal passages extending through the porous structure to intersect the internal cavity;

a first cerclage cage horizontally surrounding the porous structure; and a second cerclage cage horizontally surrounding the porous structure uncoupled from the first cerclage cage such that a longitudinal stiffness of the intervertebral implant is defined by the porous structure.

22. The intervertebral implant of claim 21, wherein the porous structure comprises:

a superior panel including a plurality of openings extending through the superior panel to partially define the plurality of longitudinal passages;

an inferior panel including a plurality of openings extending through the inferior panel to partially define the plurality of longitudinal passages; and a middle panel separating the superior panel and the inferior panel to define the interior cavity.

23. The intervertebral implant of claim 21, wherein the first cerclage cage and the second cerclage cage include ramped end portions to provide the intervertebral implant with a wedge-shaped insertion end.

24. The intervertebral implant of claim 21, wherein the first cerclage cage and the second cerclage cage each include a partial coupling socket that together form a socket configured to receive an insertion tool.

* * * * *